(12) United States Patent
Gearhart et al.

(10) Patent No.: US 6,562,619 B1
(45) Date of Patent: *May 13, 2003

(54) DIFFERENTIATION OF HUMAN EMBRYONIC GERM CELLS

(75) Inventors: John D. Gearhart, Baltimore, MD (US); Michael Joseph Shamblott, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/553,640

(22) Filed: Apr. 20, 2000

Related U.S. Application Data

(63) Continuation of application No. 09/052,772, filed on Mar. 31, 1998, now Pat. No. 6,245,566, which is a continuation-in-part of application No. 08/989,744, filed on Dec. 12, 1997, now Pat. No. 6,331,406, which is a continuation-in-part of application No. 08/829,372, filed on Mar. 31, 1997, now Pat. No. 6,090,622.

(51) Int. Cl.$^7$ .................................................. C12N 5/08
(52) U.S. Cl. ........................ 435/366; 435/325; 424/93.21
(58) Field of Search ................................ 435/325, 366, 435/440, 455; 800/8

(56) References Cited

U.S. PATENT DOCUMENTS

| | | |
|---|---|---|
| 5,035,994 A | 7/1991 | Civin |
| 5,061,620 A | 10/1991 | Tsukamoto et al. |
| 5,096,822 A | 3/1992 | Rosenkrans, Jr. et al. |
| 5,166,065 A | 11/1992 | Williams et al. |
| 5,196,315 A | 3/1993 | Ronnett et al. |
| 5,437,994 A | 8/1995 | Emerson et al. |
| 5,453,357 A | 9/1995 | Hogan |
| 5,523,226 A | 6/1996 | Wheeler |
| 5,589,376 A | 12/1996 | Anderson et al. |
| 5,591,625 A | 1/1997 | Gerson et al. |
| 5,654,183 A | 8/1997 | Anderson et al. |
| 5,670,351 A | 9/1997 | Emerson et al. |
| 5,670,372 A | 9/1997 | Hogan |
| 5,672,499 A | 9/1997 | Anderson et al. |
| 5,690,926 A | 11/1997 | Hogan |
| 5,750,397 A | 5/1998 | Tsukamoto et al. |
| 5,811,094 A | 9/1998 | Caplan et al. |
| 5,814,440 A | 9/1998 | Hill et al. |
| 5,824,489 A | 10/1998 | Anderson et al. |
| 5,843,780 A | 12/1998 | Thompson |
| 6,090,622 A * | 7/2000 | Gearhart et al. ............ 435/366 |
| 6,200,806 B1 * | 3/2001 | Thomson ................... 435/366 |
| 6,245,566 B1 * | 6/2001 | Gearhart et al. ............ 435/384 |

FOREIGN PATENT DOCUMENTS

| | | |
|---|---|---|
| EP | 0774510 A1 | 5/1997 |
| WO | 90/03432 A1 | 4/1990 |
| WO | 94/07997 | 4/1994 |
| WO | 95/10599 | 4/1995 |
| WO | 97/20035 | 6/1997 |
| WO | 97/25412 | 7/1997 |
| WO | 97/25413 | 7/1997 |

OTHER PUBLICATIONS

Beardsley, "In Focus: Culturing New Life" *Scientific American* 11–12 (1998).

Berger et al., "Self Renewal of Embryonic Stem Cells in the Absence of Feeder Cells and Exogenous Leukaemia Inhibitory Factor" *Growth Factors* 14(2–3):145–159 (1997).

Braun et al., "Myf–6, A New Member of the Human Gene Family of Myogenic Determination Factors: Evidence for a Gene Cluster on Chromosome 12" *The EMBO Journal* 9(3):821–831 (1990).

Cheng et al., "Role of Leukemia Inhibitory Factor and Its Receptor in Mouse Primordial Germ Cell Growth" *Development* 120(1):3145–3153 (1994).

Davis et al., "LIFR beta and gp130 as Heterodimerizing Signal Transducers of the Tripartite CNTF Receptor" *Science* 260(5115):1805–8 (1993).

De Felici et al., "Growth Factors in Mouse Primordial Germ Cell Migration and Proliferation" *Progress in Growth Factor Research* 5(2):135–143 (1994).

Donovan et al., "Long Term Culture of Primordial Germ Cells in Presence of Fibroblast Growth Factor and Leukaemia Inhibitory Factor, Useful in Research and Production of Chimeric and Transgenic Animals" Database WPI, Section Ch., Week 9319, Derwent Publications Ltd., London, GB; Class B04, AN 93–159486 (1993).

Donovan et al., "Primordial Germ Cells, Stem Cells and Testicular Cancer" *APMIS* 106 (1):134–141 (1998).

Durcova–Hills et al., "Short–Term Culture of Porcine Primoridal Germ Cells" *Theriogenology* 49(1):237 (1998).

Evans et al., "Derivation and Preliminary Characterization of Pluripotent Cell Lines from Procine and Bovine Blastocycts" *Theriogenology* 33(1):125–128 (1990).

Fourcin et al., "gp130 Transducing Receptor Cross–Linking Is Sufficient to Induce Interleukin–6 Type Responses" *J. Biol. Chem.* 271(20):11756–60 (1996).

R. Ian Freshney, "Culture of Animal Cells: A Manual of Basic Technique" Second Edition, Chapter 10, 1987, Alan R. Liss, Inc., New York, NY.

Jiang et al., "Cloning and Characterization of the 5' Flanking Region of the Stem Cell Factor Gene in Rat Sertoli Cells" *Gene* 185(1):285–290 (1997).

(List continued on next page.)

*Primary Examiner*—Deborah Crouch
*Assistant Examiner*—Joseph Woitach
(74) *Attorney, Agent, or Firm*—Gray Cary Ware & Freidenrich, LLP; Lisa A. Haile

(57) ABSTRACT

Primordial germ cells isolated from human embryonic tissue, such as from the gonadal ridges of human embryo, are disclosed. The primordial germ cells are cultured resulting in cells that resemble embryonic stem cells or embryonic germ cells in morphology and pluripotency. The cells are maintained several months in culture and can be genetically manipulated using transgenic technology to insert heterologous genetic material.

28 Claims, 3 Drawing Sheets

OTHER PUBLICATIONS

Keller et al., "Direct Synergistic Effects of Leukemia Inhibitory Factor on Hematopoietic Progenitor Cell Growth: Comparison With Other Hematopoietins That Use the gp130 Receptor Subunit" *Blood* 88(3):863–869 (1996).

Koshimizu et al., "Functional Requirement of gp130–Mediated Signaling for Growth and Survival of Mouse Primordial Germ Cells In Vitro and Derivation of Embryonic Germ (EG) Cells" *Development* 122(4):1235–1242 (1996).

Labosky et al., "Embryonic Germ Cell Lines and Their Derivation from Mouse Primordial Germ Cells" *Germline Development*, Wiley, Chichester (Ciba Foundation Symposium 182), pp. 157–178 (1994).

Labosky et al., "Mouse Embryonic Germ (EG) Cell Lines: Transmission Through the Germline and Differences in the Methylation Imprint of Insulin–Like Growth Factor 2 Receptor (Igf2r) Gene Compared with Embryonic Stem (ES) Cell Lines" *Development* 120(11):3197–3204 (1994).

Leslie et al., "Stimulation of DNA Synthesis in Cultured Rat Alveolar Type II Cells" *Exp. Lung Res.* 8(1):53–66 (1985) and File Server STN Karlsruhe, File Medline Abstract No. 85203765.

Lewis, "Embryonic Stem Cells Debut Amid Little Media Attention" *The Scientist* 1 (1997).

Liautard et al., "Specific Inhibition of IL–6 Signaling with Monoclonal Antibodies Against the gp130 Receptor" *Cytokine* 9(4):233–41 (1997).

Liu et al., "Interleukin–6 Signal Transducer gp130 Mediates Oncostatin M Signaling" *J. Biol Chem* 267(24):16763–6 (1992).

Matsui et al., "Derivation of Pluripotential Embryonic Stem Cells from Murine Primordial Germ Cells in Culture" *Cell* 70(5):841–847 (1992).

Modrell et al., "LIF and OM Directly Interact with a Soluble Form of gp130, the IL–6 Receptor Signal Transducing Subunit" *Growth Factors* 11(2):81–91 (1994).

Moens et al., "Ultrastructural and Immunocytochemical Analysis of Diploid Germ Cells Isolated from Fetal Rabbit Gonads" *Zygote* 5(1):47–60 (1997).

Moore, "Characterization of Porcine Inner Cell Mass (pICM) and Primordial Germ Cells (pPGC) for the Development of Transgenic Embryonic Cell Lines" *Dissertation Abstracts International* 58(11) (1998).

Ohkubo et al., "Autonomous Regulation of Proliferation and Growth Arrest in Mouse Primordial Germ Cells Studied by Mixed and Clonal Cultures" *Experimental Cell Research* 222(2):291–297 (1996).

Olie et al., "Heterogeneity in the In Vitro Survival and Proliferation of Human Seminoma Cells" *British Journal of Cancer* 71(1):13–17 (1995).

Pruss et al., "Cholera Toxin Stimulates Division of 3T3 Cells" *J. Cell Physiol* 98(3):469–74 (1979) and File Server STN Karlsruhe, File Medline Abstract No. 79173363.

Ren–Xiao et al., "Interleukin–6 Receptor Antagonists Inhibit Interleukin–11 Biological Activity" *Eur Cytokine Netw* 8(1):51–6 (Mar. 1997).

Resnick et al., "Long–term Proliferation of Mouse Primordial Germ Cells in Culture" *Nature* 359(6395):550–551 (1992).

Rohwedel et al., "Primordial Germ Cell–Derived Mouse Embryonic Germ (EG) Cells In Vitro Resemble Undifferentiated Stem Cells with Respect To Differentiation Capacity and Cell Cycle Distribution" *Cell Biology International* 20(8):579–587 (1996).

Schuldiner et al., "Effects of Eight Growth Factors on the Differentiation of Cells Derived from Human Embryonic Stem Cells" *PNAS* 97.(21):11307–11312 (2000).

Shamblott et al., "Derivation of Pluripotent Stem Cells from Cultured Human Primordial Germ Cells" *Proc. Natl. Acad. Sci USA* 95:13726–13731 (1998).

Shamblott et al., "Human Embryonic Germ Cell Derivatives Express a Broad Range of Developmentally Distinct Markers and Proliferate Extensively In Vitro" *PNAS* 98(1):113–118 (2001).

Shamblott et al., "Pluripotent Stem Cells" *Prin. Of Tissue Engineering*, $2^{nd}$ Ed., Chap. 29:369–381 Academic Press (2000).

Shim et al., "Isolation of Pluripotent Stem Cells from Cultured Porcine Primordial Germ Cells" *Biology of Reproduction* 57:1089–1095 (1997).

Shuldiner et al., "Effects of Eight Growth Factors on the Differentiation of Cells Derived from Human Embryonic Stem Cells" *PNAS* 97(21):11307–11312 (2000).

Smith, "Culture and Differentiation of Embryonic Stem Cells" *J. Tissue Culture Method* 13:89–94 (1991).

Smith et al., "Buffalo Rat Liver Cells Produce a Diffusible Activity Which Inhibits the Differentiation of Murine Embryonal Carcinoma and Embryonic Stem Cells" *Development Biology* 121(1):1–9 (1987).

T. Taga, "Gp130, a Shared Signal Transducing Receptor Component for Hematopoietic and Neuropoietic Cytokines" *J. Neurochem* 67(1):1–10 (1996).

Taylor et al., "Human Stem Cell Factor Promoter Dexoyribononucleic Acid Sequence and Regulation by Cyclic 3',5 '–Adenosine Monophosphate in a Sertoli Cell Line" *Endocrinology* 137(12):5407–5414 (1996).

Thomson et al., "Embryonic Stem Cell Lines Derived from Human Blastocysts" *Science* 282:1145–1147 (1998).

Thomson et al., "Isolation of a Primate Embryonic Stem Cell Line" *Proc. Natl. Acad. Sci. USA* 92(17):7844–7848 (1995).

Tohyama et al., "Nestin Expression in Embryonic Human Neuroepithelium and in Human Neuroepithelial Tumor Cells" *Laboratory Investigation* 66(3):303–313 (1992).

Topp et al., "In Vitro Differentiation of Teratomas and the Distribution of Creatine Phosphokinase and Plasminogen Activaor in Teratocarcinoma–Derived Cells" *Cancer Research* 36:4217–4223 (1976).

Uchida et al., "Effects of Feeder Cells and Growth Factors on the Proliferation of Mouse Primordial Germ Cells" *Therigenology* 44(1):9–16 (1995).

Wijdenes et al., "Interleukin–6 Signal Transducer gp130 Has Specific Binding Sites for Different Cytokines as Determined by Antagonistic and Agonistic Anti–gp130 Monoclonal Antibodies" *Eur. J. Immunol.* 25(12):3474–81 (1995).

Wobus et al., "In Vitro Differentiation of Embryonic Stem Cells into Cardiomyocytes or Skeletal Muscle Cells Is Specifically Modulated by Retinoic Acid" *Roux's Arch. Dev. Biol* 204(1):36–45 (1994).

Yuen et al., "Generation of a Primitive Erythroid Cell Line and Promotion of Its Growth by Basic Fibroblast Growth Factor" *Blood* 91(9):3202–3209 (1998).

Shamblott, Michael J. et al., "Properties of Cell Lines-Derived from Human Primordial Germ Cells," *Molecular Biology of the Cell*, vol. 8, p. 223A, Nov. 1997.

Wang, S. et al., "Neural Cells Derived in Culture from Human Embryonic Germ (EG) Cells," *Molecular Biology of the Cell*, vol. 9, p. 437A, Nov. 1998.

* cited by examiner

DIFFERENTIATION OF HUMAN EMBRYONIC GERM CELLS

CROSS-REFERENCE TO RELATED APPLICATIONS

This application is a continuation application of U.S. application Ser. No. 09/052,772, filed Mar. 31, 1998, which is a continuation-in-part application of U.S. application Ser. No. 08/989,744, filed Dec. 12, 1997, which is a continuation-in-part application of U.S. application Ser. No. 08/829,372, filed Mar. 31, 1997, now issued as U.S. Pat. No. 6,090,622. The disclosure of each of the prior applications is considered part of and is incorporated by reference in the disclosure of this application.

BACKGROUND OF THE INVENTION

1. Field of the Invention

The present invention relates generally to the field of in vitro culture of undifferentiated cells and methods of producing such cells. More specifically the invention relates to methods and compositions for producing human embryonic germ (EG) cells and methods of using such cells. The invention has applications in the areas of cell culture, tissue transplantation, drug discovery, and gene therapy.

2. Description of Related Art

Pluripotent embryonic stem cells have traditionally been derived principally from two embryonic sources. One type of mouse pluripotent cell can be isolated in culture from cells of the inner cell mass of a pre-implantation embryo and are termed embryonic stem (ES) cells (Evans & Kaufman, Nature 292: 154–156, 1981). A second type of mouse pluripotent stem cell can be isolated from primordial germ cells (PGCs) located in the mesenteric or genital ridges of days 8.5–12.5 post coitum mouse embryos and has been termed embryonic germ cell (EG) (Matsui et al., Nature 353:750–751, 1991; Resnick et al., Nature 359:550–551, 1992; Hogan, U.S. Pat. No. 5,453,357). Both types of cells are pluripotent and demonstrate germline genetic transmission in the mouse.

ES and EG cells propagated in vitro can contribute efficiently to the formation of chimeras, including germline chimeras. Importantly, both of these cell types can be genetically manipulated in vitro without losing their capacity to generate germline chimeras.

Thus, ES and EG cells are useful in methods for the generation of transgenic animals. Such methods have a number of advantages as compared with more conventional techniques for introducing new genetic material into such animals, such as zygote injection and viral infection. First, the gene of interest can be introduced and its integration and expression characterized in vitro. Second, the effect of the introduced gene on the ES or EG growth can be studied in vitro. Third, the characterized ES or EG cells having the novel genes can be efficiently introduced into embryos by blastocyst injection or embryo aggregation, and the consequences of the introduced gene on the development of the resulting transgenic chimeras monitored during prenatal or postnatal life. Fourth, the site in the ES or EG genome at which the introduced gene integrates can be specified, permitting subsequent gene targeting and gene replacement (Thomas & Capecci, Cell 51:5003–512, 1987).

However, the EG or ES cell lines studied to-date only retain the stem cell phenotype in vitro when cultured under special conditions. The conditions include culturing the cells on a feeder layer of fibroblasts (such as murine STO cells, e.g., Martin & Evans, Proc. Natl. Acad. Sci. USA 72:1441–1445, 1975) when cultured in medium conditioned by certain cells (e.g. Koopman & Cotton, Exp. Cell 154:233–242, 1984; Smith & Hooper, Devel. Biol. 121:1–91, 1987), or by the exogenous addition of leukemia inhibitory factor (LIF). Such cells can be grown relatively indefinitely using the appropriate culture conditions. However, the factors responsible for maintaining the pluripotency of ES and EG cells remain poorly characterized and are often dependent upon the species from which the cells have been harvested.

In the absence of feeder cells, exogenous leukemia inhibitory factor (LIF), or conditioned medium, ES or EG cells spontaneously differentiate into a wide variety of cell types, including cells found in each of the endoderm, mesoderm, and ectoderm germ layers. With the appropriate combinations of growth and differentiation factors, however, cell differentiation can be controlled. For example, mouse ES and EG cells can generate cells of the hematopoietic lineage in vitro (Keller et al., Mol. Cell. Biol. 13:473–486, 1993; Palacios et al., Proc. Natl. Acad. Sci. USA 92:7530–7534, 1995; Rich, Blood 86:463–472, 1995). Additionally, mouse ES cells have been used to generate in vitro cultures of neurons (Bain et al., Developmental Biology 168:342–357, 1995; Fraichard et al. J. Cell Science 108:3161–3188, 1995), cardiomyocytes (heart muscle cells) (Klug et al., Am. J. Physiol. 269:H1913–H1921, 1995), skeletal muscle cells (Rohwedel et al., Dev. Biol. 164:87–101, 1994), and vascular cells (Wang et al., Development 114:303–316, 1992).

Subsequent to the work with mouse embryos, several groups have attempted to develop similar embryonic stem cell lines from sheep, pig, and cow. A cell line with embryonic stem cell-like appearance has reportedly been cultured from porcine embryos using culture conditions similar to mouse (Evans et al., PCT Application WO90/03432; Notarianni et al., J. Reprod Fert., Suppl. 41:51, 1990; Piedrahita et al., Theriogenology 34:879, 1990; Notarianniet et al., Proceedings of the 4th World Congress on Genetics Applied to Livestock Productions, 58, Edinburgh, July 1990). Other groups have developed avian stem cell lines from chickens (Pain et al., Development, 122:1996). However, human ES and EG cell lines have not been reported.

Any method that would allow production of human ES and EG is desirable, since human ES or EG cell lines would permit easier study of early human development, and the use of such human EG cell lines would enable the development of cell cultures for transplantation, manufacture of biopharmaceutical products, and development of biological-based sensors. Importantly, the ability to produce large quantities of human cells has important working applications for the production of substances, such as insulin or factor VIII which currently must be obtained from non-human sources or donors; implantation to treat disease, such as Parkinson's disease; tissue for grafting; and screens for drugs and toxins.

SUMMARY OF THE INVENTION

The present invention provides a human embryonic pluripotent germ cell (EG) line and a method of producing such cells. The invention also provides methods of using EG cells.

EG cells are derived from primordial germ cells (PGCS) cells isolated, according to one embodiment, from gonadal tissues, genital ridges, mesenteries or embryonic yolk sacs of human embryos. The PGCs are cultured under conditions that allow derivation of EG cells. The present invention also provides cell culture media for long term cell culture (more than 30 days) of the resulting EG cells.

The invention provides a cell line having the characteristics of a human embryonic germ cell. In one aspect, the cells are cultured in a medium including a growth factor, e.g., basic fibroblast growth factor (bFGF). In another embodiment, the cells are cultured in the presence of culture media containing an effective amount of either a ligand that binds to a receptor which can associate with glycoprotein 130 (gp130) or an antibody that binds to and stimulates gp130; and a growth factor, which in one embodiment is bFGF. In another embodiment, the EG cell culture medium of the invention can include forskolin or other cAMP elevating compound. In another aspect, the EG cells are alkaline phosphatase positive. In yet another aspect, the EG cells express cell surface antigens SSEA-1 and SSEA-4. In still another aspect, the EG cells express cell surface antigens that bind with antibodies having the binding specificity of monoclonal antibodies TRA-1-60 (ATCC HB-4783) and TRA-1-81 (ATCC HB-4784). The cells can also express cell surface antigen SSEA-3.

In one aspect, the invention provides a method for screening to identify compounds that affect EG cell function. In one embodiment, the method includes incubating components comprising the compound and at least one EG cell under conditions sufficient to allow the compound and cell to interact; and determining the effect of the compound on an EG cell function before and after incubating in the presence of the compound. A cell function that may be modulated (e.g., inhibited or stimulated) by the compound includes, but is not limited to, differentiation, gene expression, production of growth factors, response to growth factors and modulation of cell membrane permeability. In another aspect, the present invention provides useful pharmaceutical products produced by the EG cells or cell lines derived from the EG cells of the present invention, including cells and cell lines derived from EG cells comprising one or more genetic modifications.

In another aspect, the invention provides a method of using an EG cell to produce restricted developmental lineage cells. In one embodiment, an EG cell is cultured under conditions effective to induce differentiation of the EG cell to produce thereby a cell of restricted developmental lineage from the EG cell. In one embodiment, the agent is a polypeptide inducibly or constitutively expressed from a stably transfected recombinant polynucleotide in the EG cell. For example, a recombinant telomerase is expressed in a restricted developmental lineage cell, thereby producing immortalized human cells having the characteristics of a restricted developmental lineage cell.

In another aspect, a selectable marker is expressed in a restricted developmental lineage cell. The restricted developmental lineage cell contains a recombinant polynucleotide that encodes the selectable marker such that the marker is expressed from a restricted developmental lineage cell specific promoter. The restricted developmental lineage cells may be neuroepithelial cells (e.g., neurons, glia, or epithelial cells) or myocytes (e.g., cardiomyocytes or skeletal muscle cells). Thus, in one embodiment, the invention provides a method of using an EG cell to produce a neural network. In another embodiment, the invention provides a method of using an EG cell to produce neuro muscular junctions.

In another embodiment, the invention provides a method for identifying a compound that can cause EG cells to differentiate. In one embodiment of the method, components including the compound and at least one EG cell are incubated under conditions sufficient to allow the components to interact. The effect of the compound on the EG cell is determined before and after incubating in the presence of the compound. The appearance in culture of a restricted developmental lineage cell indicates differentiation of the EG cell by the compound.

In another embodiment, the invention provides a method for identifying a compound that can de-differentiate a restricted developmental lineage cell to provide an EG cell. In one embodiment of the method, components, including the compound and at least one human restricted developmental lineage cell, are incubated under conditions sufficient to allow the components to interact. The effect of the compound on the human restricted developmental lineage cell is determined before and after incubating in the presence of the compound. The appearance in culture of a cell having the characteristics of an EG cell indicates the compound is effective to induce de-differentiation of the restricted developmental lineage cell.

DETAILED DESCRIPTION OF THE INVENTION

Figure 1A:
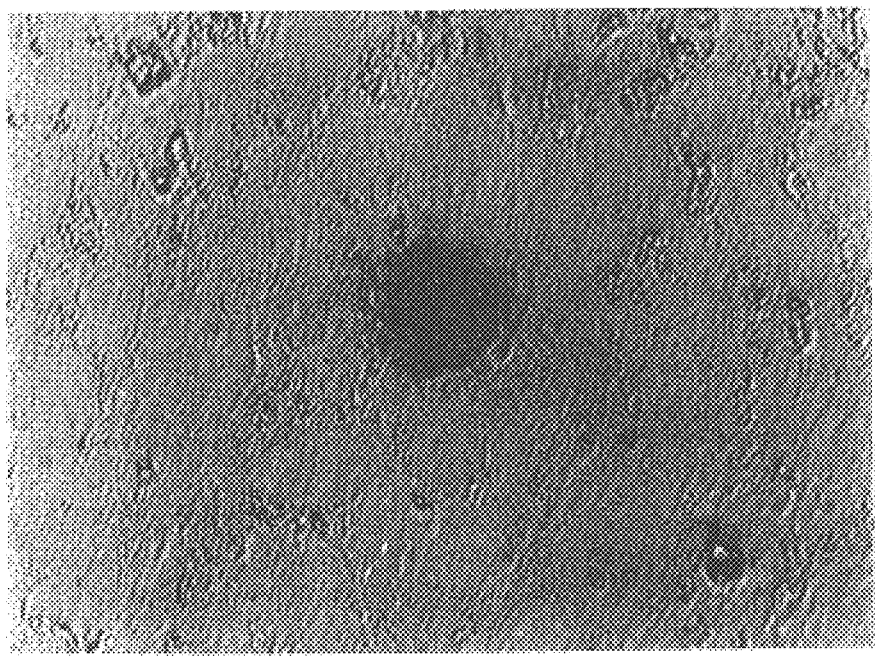
FIGS. 1a and b show potomicrographs of human embryonic germ cells (EGs) showing positive histological staining for alkaline phosphatase.

The present invention provides human EG cells and of methods of producing and maintaining such human EG cells in culture. An advantage of the invention is that human EG cells can be efficiently produced. The development of EG cell cultures that can be maintained as cell lines permits investigation of fundamental questions regarding the biochemical and cellular properties of these cells and the dynamics of interaction in their cellular and chemical environment. In addition, useful tissues and substances can be produced using the human EG cells of the invention.

As one example, the EG cells of the invention can advantageously be used to stably incorporate genetic sequences encoding various receptors, ligands and neurotransmitters, for example, for use in the treatment of subjects with various disorders and for identifying compounds and small molecules that interact with the genetically modified cells or the EG cells themselves.

This invention is not limited to the cells, compositions, reagents, methods or uses described, as such cells, compositions, reagents, methods or uses may, of course, vary. The terminology used herein is for the purpose of describing particular embodiments only, and the terminology used herein is not intended to limit the scope of the present invention, which will only be limited by the appended claims.

All references cited herein are hereby incorporated by reference in their entirety. Nothing herein is to be construed as an admission that the invention is not entitled to antedate such disclosure by virtue of prior invention. Throughout this description, the preferred embodiment and examples shown should be considered as exemplars, rather than as limitations on the present invention.

Definitions

The following terms will be defined as provided unless otherwise stated. All other terminology used herein will be defined with respect to its usage in the particular art to which it pertains unless otherwise noted.

An "anlagen" is the rudiment or the primordia of an organ, tissue or part thereof.

The term "antibody" as used in this invention includes intact molecules as well as fragments thereof, such as Fab, Fab', F(ab')$_2$, and Fv that can bind the epitopic determinant. If needed, polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies.(See, e.g., Coligan, et al., *Current Protocols in Immunology*, Wiley Interscience, current edition, incorporated by reference). "Purified antibody" means an antibody that is at least 60%, by weight, free from proteins and naturally-occurring organic molecules with which it is naturally associated. Preferably, the preparation is at least 75%, more preferably 90%, and most preferably at least 99%, by weight, antibody, e.g., an anti-SSEA-1 specific antibody. A purified antibody may be obtained, for example, by affinity chromatography using recombinantly-produced protein or conserved motif peptides and standard techniques. The invention can employ not only intact monoclonal or polyclonal antibodies, but also an immunologically-active antibody fragment, such as a Fab, Fab' or (Fab')$_2$ fragments, or a genetically engineered Fv fragment (Ladner et al., U.S. Pat. No. 4,946,788).

The term "cell" as used herein also refers to individual cells, cell lines, or cultures derived from such cells. The term "cell line" as used herein refers to human EG cells or cells derived therefrom such as are maintained in in vitro culture.

"EG culture medium" or "EG growth medium" means a suitable medium capable of supporting growth of human EG cells. Examples of suitable culture media useful in practicing the present invention are a variety of human EG growth media prepared with a base of Dulbecco's minimal essential media (DMEM) supplemented with 15% fetal calf serum, 2 mM glutamine, 1 mM sodium pyruvate, or glucose and phosphate free modified human tubal fluid media (HTF) supplemented with 15% fetal calf serum, 0.2 mM glutamine, 0.5 mM taurine, and 0.01 mM each of the following amino acids; asparagine, glycine, glutamic acid, cysteine, lysine, proline, serine, histidine, and aspartic acid (McKieman et al., *Molecular Reproduction and Development* 42:188–199, 1995). Typically, the EG medium also contains commonly used tissue culture antibiotics, such as penicillin and streptomycin. An effective amount of factors are then added daily to either of these base solutions to prepare human EG growth media of the instant invention. The term "effective amount" as used herein is the amount of such described factor as to permit a beneficial effect on human EG growth and viability of human EG cells using judgement common to those of skill in the art of cell culturing and by the teachings supplied herein.

"Conditioned medium" refers to a growth medium that is further supplemented by factors derived from media obtained from cultures of feeder cells on which human EG cells can be cultured.

"Detectably-labeled" refers to any means for marking and identifying the presence of a cell or part thereof, i.e., an oligonucleotide probe or primer, an antibody or fragment thereof, a protein or fragment thereof, a gene or fragment thereof, or a cDNA molecule. Methods for detectably-labeling cells or molecules are well known in the art and include, without limitation, radioactive labeling (e.g., with an isotope such as $^{32}$P or $^{35}$S) and nonradioactive labeling (e.g., chemiluminescent labeling, fluorescent labeling, enzymatic reaction products coded by genes, i.e., CAT).

"Embryonic germ cells" or "EG cells" are cells derived from primordial germ cells (PGCs). The term "embryonic germ cell" is used to describe cells of the present invention that exhibit an embryonic pluripotent cell phenotype. The terms "human embryonic germ cell (EG)" or "embryonic germ cell" can be used interchangeably herein to describe human cells, or cell lines thereof, of the present invention that exhibit a pluripotent embryonic stem cell phenotype as defined hereinbelow. Thus, EG cells are capable of differentiation into cells of ectodermal, endodermal, and mesodermal germ layers. EG cells can also be characterized by the presence or absence of markers associated with specific epitope sites identified by the binding of particular antibodies and the absence of certain markers as identified by the lack of binding of certain antibodies.

"Epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

"Growth factor" as used for the purposes of describing the present invention refers to a substance that is effective to promote the growth of human EG cells that is not otherwise a component of the growth medium. Such substances include, but are not limited to, cytokines, chemokines, small molecules, neutralizing antibodies, and proteins. Growth factors also include intercellular signaling polypeptides which control both the development and maintenance of cells, and the form and function of tissues.

"Non-essential Amino acids" refers to the amino acids L-alanine, L-asparagine, L-aspartic acid, L-glutamic acid, glycine, L-proline, and L-serine.

The term "primordial germ cells" (PGCs) is used to descibe undifferentiated embryonic germ cells isolated over a period of time post-fertilization from anlagen or from yolk sac, mesenteries, or gonadal ridges of human embryos/fetus. PGCs are the source from which EG cells are derived. Gonocytes of later testicular stages also can be useful sources of PGCs.

"Pluripotent" refers to cells that retain the developmental potential to differentiate into a wide range of cell lineages including the germ line. The terms "embryonic stem cell phenotype" and "embryonic stem-like cell" also are used interchangeably herein to describe cells that are undifferentiated and thus are pluripotent cells and that are capable of being visually distinguished from other adult cells of the same animal.

The term "STO cell" refers to embryonic fibroblast mouse cells such as are commercially available and include those deposited as ATCC CRL 1503.

"Transplants" include cells (or parts thereof), cell products, tissue, or cell culture products derived from EG cells that are grafted into a human host. Specifically, a transplant is produced by manipulating EG cells, which exhibit a pluripotent embryonic germ cell phenotype, in vitro to produce EG derived stem cells of restricted developmental lineage. The term "restricted developmental lineage" means that the prospective fate of the stem cells derived from the EG cell is reduced to a smaller number of possible histotypes after induction of differentiation. Methods of inducing in vitro differentiation of EG cells include using retinoic acid or the removal of cell feeder layers or conditioned media as described herein. The resulting stem cells of restricted developmental lineage can be further manipulated to include exogenous genetic material such as a transgene. Provided that the cell expressing an EG phenotype is genetically manipulated to include exogenous material, the resulting transplant can include exogenous material within some, but not all of its cells. Resulting transplant cell lines of restricted developmental lineage can be maintained or further manipulated as pure cell lines by techniques common to those in the art.

"Transgene" means any piece of DNA inserted by artifice into a cell that becomes part of the genome of the cell, cell line, tissue or organism (i.e., either stably integrated or as a stable extrachromosomal element) which develops from that cell. Such a transgene may include a gene which is partly or entirely heterologous (i.e., foreign) to the cell or organism to which the heterologous gene is introduced, or may represent a gene homologous to an endogenous gene of the organism. Included within this definition is a transgene created by the providing of an RNA sequence that is transcribed into DNA and then incorporated into the genome.

The term "transgenic" includes any transgenic technology familiar to those in the art which can produce an organism, cell, cell culture, cell line, tissue or embryo carrying an introduced transgene or one in which an endogenous gene has been rendered nonfunctional or "knocked out." A "transgenic" is an animal or any part thereof, including, but not restricted, to cells, cultures or tissues which includes exogenous genetic material within its cells. Cells of the invention can have DNA added to them and these cells can then be used in a manner similar to that for making a chimeric organism.

The term "gene knockout" as used herein, refers to the targeted disruption of a gene with either partial or complete loss of function achieved by any transgenic technology familiar to those in the art. For example, transgenic cells having gene knockouts are those in which the target gene has been rendered nonfunctional by an insertion targeted to the gene to be rendered nonfunctional by homologous recombination.

"Transfected" means a cell into which (or into an ancestor of which) has been introduced, by means of any recombinant nucleic acid techniques known to those in the art, a heterologous nucleic acid molecule. "Heterologous nucleic acid" refers to a nucleic acid sequence that either originates from another species or is modified from either its original form or the form primarily expressed in a cell.

Embryonic Germ Cells and Methods of Culture

In one embodiment, the invention provides human EG cells and a method of producing such cells. A starting material for isolating the cells may be primordial germ cells (PGCs) isolated over a period of about 9 weeks to about 11 weeks from the last menstrual period (LMP) (3–13 weeks post-fertilization), from embryonic yolk sac, mesenteries, gonadal anlagen, or genital ridges from human embryos/fetus. Alternatively, gonocytes of later testicular stages can also provide PGCs. In one embodiment, the PGCs are cultured on mitotically inactivated fibroblast cells (e.g., STO cells) under conditions effective to derive EGs. The resulting human EG cells resemble murine ES or EG cells in morphology and in biochemical histotype. The resulting human EG cells can be passaged and maintained for at least several months in culture.

In culturing the EG cells of the invention, it is believed that the use of feeder cells, or an extracellular matrix derived from feeder cells, provides one or more substances necessary to promote the growth of EG cells and/or prevents or inhibits the rate of differentiation of such cells. Such substances are believed to include membrane-bound and/or soluble cell products that are secreted into the surrounding medium by the cells. For example, EG cells can be grown on a substrate selected from the group consisting of mouse embryo fibroblast cells, STO cells, human fibroblasts, or human epithelium cells. Thus, those of skill in the art will recognize that additional cell lines can be used with the cell culture medium to equivalent effect and that such additional cell lines can be identified using standard methods and materials. In addition, those of skill in the art will also recognize that one or more substances produced by the feeder cells, or contained in the extracellular matrix, can be identified and added to the cell culture medium of the invention to obviate the need for such feeder cells and/or such extracellular matrix.

Using the methods and materials described herein, two human pluripotential embryonic germ cell (EG) cultures, designated hEG-KH and hEG-GU, have been derived and cultured. The hEG-KH and hEG-GU cell cultures were derived from the gonadal anlagen and genital rides of approximately 8 and 11-week last menstrual period (LMP) aborted human fetal material, respectively.

The EG is pluripotent and is characterized by the presence of markers associated with specific epitopic sites that can be identified by the binding of particular antibodies, and the absence of certain markers that can be identified by the lack of binding of certain antibodies. EG cells also expresses cell surface antigens SSEA-1 and SSEA-4 and express cell surface antigens that bind to antibodies having the binding specificity of monoclonal antibodies TRA-1-60 (ATCC HB-4783) and TRA-1-81(ATCC HB-4784). EG cells of the invention can also express the cell surface antigen SSEA-3.

In addition, EG cells stain positively for alkaline phosphatase (AP) activity.

Cell Culture Media

The invention utilizes cell culture media, growth factors, and methods for growing and maintaining cultures of EG cells. The media provides for the growth and maintenance of EG cells and can be used to screen for additional growth factors and useful combinations of growth factors. The ability to grow EG cells in a substantially undifferentiated state using the cell culture media, growth factors, and methods provided herein provides important benefits including the ability to produce EG cell lines having multiple genetic modifications having important therapeutic applications as discussed below.

The cell culture media may include a growth medium that is effective to support the growth of EG cells; a nutrient serum effective to support the growth of EG cells; non-essential and essential amino acids, and a pyruvate salt. Optionally, the cell culture media may also include a reducing agent.

The growth medium can include any serum or serum-based solution that supplies nutrients effective to maintain the growth and viability of EG cells. Examples of such serum include, without limitation, fetal bovine serum (FBS) and fetal calf serum (FCS). For example, the FBS may be provided in a concentration of between about 1% and about 25%. In particular, the FBS may be provided in a concentration of between about 2.5% and about 20%. In one embodiment, EG cells are grown in 15% FBS.

The EG may be dependent on some growth factors for maintenance in the cultured state. In one embodiment the growth factor is basic fibroblast growth factor (bFGF). In another embodiment, a ligand which binds to a receptor on EG that can associate with glycoprotein 130 (gp130) is included in the culture media. In a more particular embodiment, the ligand is oncostatin-M or leukemia inhibitory factor (LIF). In addition, an antibody that binds to, and activates, gp130 directly can be used.

A growth factor may also be provided to assist in the derivation and maintenance of cultures of EG cells in a substantially undifferentiated state. The identities and effective concentrations of such growth factors can be determined using the methods as described herein or using techniques known to those of skill in the art of culturing cells. For example, one or more of the following factors can be used at the stated final concentration: forskolin ([3R-(3$\alpha$, 4$\alpha\beta$, 5B, 6B, 6a$\alpha$, 10$\alpha$, 10$\alpha\beta$, 10$\alpha$)]-5-(acetyloxy)-3-ethenyldodecahydro-6, 10, 10b-trihydroxy-3, 4a, 7, 7, 10a-pentamethyl-1H-naphtho[2,1-b]pyran-1-one) at 10 $\mu$M, cholera toxin at 10 $\mu$M, isobutylmethylxanthine (IBMX) at 0.1 mM, dibutyrladenosine cyclic monophosphate (dbcAMP) at 1 mM. In another embodiment, the growth factor is basic fibroblast growth factor (bFGF), more specifically, human recombinant basic fibroblast growth factor (bFGF), in the range of about 1–10 ng/ml.

The EG cells can be grown on the plate in addition to the feeder cells. Alternatively, the feeder cells can be first grown to confluence and then mitotically inactivated (e.g., by irradiation) to prevent further growth. Such an approach has the advantage of simplifying the management of the cell culture as the growth of only one set of cells, the EG cells, need only be monitored.

Another factor is growth media harvested from cultures of human embryonal carcinoma (EC) cells. In a particular example, human NTERA-2 EC cells (ATCC accession number CRL 1973) are grown to confluence in DMEM supplemented with 10% fetal calf serum or mouse ES cells are grown to confluence in DMEM supplemented with 15% fetal calf serum, 2 mM glutamine, 1000 U/ml LIF. Growth media is harvested daily over several days, passed through a 0.22 micron filter and frozen at –80° C. This human EC or mouse ES "conditioned" media is added to the EG growth media in empirically determined amounts, as judged by the effect on EG growth and viability.

In another embodiment the growth media includes ligands for receptors that activate the signal transduction gp130, either by binding to a receptor that associates with gp 130 or by binding directly to and activating gp 130. For example, human recombinant leukemia inhibitory factor (LIF) at about 1000 U/ml to 2000 U/ml or oncostatin-M at 10 U/ml, can be used.

Once established, the EG cells can be cultured under the above-described conditioned medium using a variety of techniques. In one example, a container holds feeder cells in a non-conditioned medium. A matrix of lysed feeder cells is prepared using standard methods. The EG cells to be cultured are then added atop the matrix along with the conditioned medium. Alternatively, the EG cells can be grown on living feeder cells using methods known in the art. The growth of the EG cells is then monitored to determine the deep to which the cultured cells have become differentiated. A marker for alkaline phosphatase can be used to ascertain which cells have differentiated. When a sufficient number of cells have differentiated, or when the culture has grown to confluence, at least a portion of the undifferentiated cells can be passaged. The determination to passage the cells and the techniques for accomplishing such passaging can be performed using standard techniques well known in the art.

Use of EG Cells To Produce cDNA Libraries

EG cells of the present invention are a plentiful source of pluripotent cell mRNA to create cDNA libraries and templates for polymerase chain reaction based experimentation. For example, EG lines are cultured in the presence of irradiated mouse STO fibroblasts as described above. Several steps are taken to eliminate STO cells and STO cDNA. In one embodiment, STO cells are removed as follows. Approximately $10^6$ EG cells growing on irradiated STO fibroblasts are trypsinized and resuspended in EG media. The resuspended cells are plated on a tissue culture dish and allowed to sit for about 1 hour. During this time, STO fibroblasts adhere while EG cells do not. Unattached cells are gently removed and the plating procedure is repeated twice. This series of preferential bindings effectively removes 50–90% of STO cells. The remaining EG cells are spun at 1000 rpm for 5 minutes, and the pellet is used to generate RNA, mRNA and then cDNA. The cDNA is subjected to several rounds of subtraction using STO cell RNA, by a commonly described methodology (Maniatis, et al., *Molecular Cloning: A Laboratory Manual*, Cold Spring Harbor Laboratory, Cold Spring Harbor, N.Y., current edition, incorporated herein by reference in its entirety). This removes STO and fibroblast cDNAs. The remaining cDNA is enriched for the human cDNAs unique to pluripotent cells. Many cDNA library screenings can be employed on this cDNA library, as well as other DNA subtractions commonly known to those in the art (Maniatis, et al., *Molecular Cloning: A Laboratory Manual*, Cold Spring Harbor Laboratory, Cold Spring Harbor, N.Y., current edition, incorporated herein by reference, in its entirety).

Production of Immortalized Human Differentiated Cells by Telomerase Transfection All normal somatic living cells exhibit the Hayflick limit—a finite number of replications after which the cells enter a senescent, nondividing phase. The Hayflick limit results from progressive shortening of telomere lengths (chromosome tips) with each replicative division. The enzyme telomerase has been shown to restore the length of telomeres, when transfected into normal dividing cells and extends their replicative lifespan indefinitely without causing malignant transformation (Bodnar et al. *Science*, 279: 349–352, 1998). This technology enables one to immortalize virtually any cell in the body without altering its normal physiology.

Although human EG cells express telomerase activity, it may be desirable to enhance such expression by transfection of EG cells with the for telomerase. Alternatively, it may be desirable to produce cells derived from EGs that also display telomerase activity, and more particularly, telomerase activity that can be induced or suppressed under controlled conditions. Thus, the present invention includes EGs transfected with telomerase as well as cells derived from such transfected EG cells. The present invention further includes EG cells transfected with telomerase that is inducible or suppressible.

EG Cells Having Multiple Genetic Modifications

In one aspect, the methods and culture media of the present invention are used to produce EG cells having multiple genetic modifications. Multiple genetic alteration of cells is desirable for many reasons, such as providing modified cells for gene therapy and replacement tissues for grafting or implantation (e.g., to avoid host rejection of the cells). This application can be used to model or treat contiguous gene disorders, aneuploidy or other large-scale chromosomal phenomenon.

In another embodiment and use of the invention, multiple changes are made to the EG genome using the above mentioned techniques. Serial transgenic events using different drug selection genes in each construct, followed by appropriate drug selection of the cells, can be used to accomplish this.

Large-scale genetic manipulation of the EG genome is another use of the invention. Large (3–4cM) chromosomal regions can be deleted, inverted, translocated, and duplicated using cre/LoxP mediated chromosome engineering (Ramirez-Solis et al., *Nature*, 378:720–724, 1995). Homologous recombination or random insertional transgenesis techniques are used to serially integrate small genetic elements termed loxP sites into an EG cell genome. The cells are then treated with cre protein administered by lipofection or transient transfection. The EG cells can then be maintained in an undifferentiated state or allowed to differentiate as described below. Tissue- and developmental-specific expression of cre can be accomplished using this technique.

Genetic constructs are introduced into EG cells by electroporation, calcium phosphate, microinjection, lipofection, retroviral or other viral or microbial vector or other means. By design, the constructs are not integrated into the EG genome or stably propagated as an episome. These constructs have a transient effect on EG cells. Alternatively, the constructs are allowed to incorporate stably into the EG genome.

For example, EG cells are grown using the culture media and methods described herein. A first gene in at least one of the cells of the cell culture is modified and from the resulting culture a first clone population of modified EG cells is derived. The first clone population is grown in the culture media of the invention and a second gene in at least one cell of the first clone population is modified to produce a second clone population having modified the first and second genes.

The methods used to perform the genetic modifications to the cells can be any of those known in the molecular biological arts for making genetic alternations. Such methods include, but are not limited to, the use of positive-negative selector vectors as described in U.S. Pat. Nos. 5,464,764; 5,487,992; 5,627,059; and 5,631,153 to Capecchi, et al.; and U.S. patent application Ser. No. 08/781,559. In addition, yeast artificial chromosomes (YACs) can be employed to perform genetic modifications as described in U.S. patent application Ser. Nos. 08/597,532; 08/397,547; 08/187,161; 08/276,565; 08/375,482; 08/485,505; and 08/372,482. Furthermore, isogenic DNA constructs, can be used with the EG cells cultured using the methods and materials. provided by the present invention as described in U.S. patent application Ser. No. 08/563,138. Still other methods include those described in U.S. Pat. No. 5,591,625 to Gerson, et al., for the preparation stem cells capable of augmented expression of certain gene products, signal transduction molecules, cell surface proteins and the like for therapeutic applications. These patents and patent applications are incorporated herein by reference in their entirety and for all purposes.

A reporter gene can be incorporated into the DNA of an EG cell that is functionally coupled with a copy of a gene associated with a particular disease state (e.g. BRCA-1 in the case of breast cancer). In one example, the reporter is sensitive to both transcription and post-transcription events. The EG cells are allowed to differentiate such that the differentiated progeny each contain one copy of the disease gene/reporter construct. Alternatively, one genetic manipulation can be the incorporation of telomerase activity as described above.

Screens for Culture Media Factors

In another embodiment and use of the invention, EG cells are used to optimize the in vitro growth and culture conditions for undifferentiated EG and their differentiating and differentiated derivatives. High-throughput screens can be established to assess the effects of media components, exogenous growth factors, and attachment substrates. These substrates include viable cell feeder layers, cell extracts, defined extracellular matrix components, substrates which promote three-dimensional growth such as methylcellulose and collagen, novel cell attachment molecules, and/or matrices with growth factors or other signaling molecules embedded within them. This last approach may provide the spatial organization required for replication of complex organ architecture (for review, see Saltzman et al, *Nature Medicine*, 4:272–273, 1998). A variety of components can be measured to quantify the effects of the experimental treatment. These include the alkaline phosphatase activity of undifferentiated EG, substances produced by differentiating or differentiated derivatives, or reporter molecules. EG and derivatives gradually adapt to convenient or experimentally essential growth conditions, such as reduced requirement for LIF and feeder layers. This allows the testing of dissociation enzymes that allow efficient passage but do not destroy essential cell surface molecules.

In another aspect, the present invention provides screens for determining growth factors that promote or inhibit the differentiation of EG cells in culture. The presence of increased alkaline phosphatase activity indicates that the substance being tested is a growth factor.

The level of expression of alkaline phosphatase can be determined for each group of cells exposed to a particular putative growth factor using the methods described herein, and correlated with increased alkaline phosphatase expression relative to control cells not exposed to a putative growth factor. In one embodiment, substances found to produce an increase of alkaline phosphatase expression greater than about 20% as compared with the control are considered growth factors.

Substances identified as growth factors screen can be tested in a secondary screen to determine the presence or absence of a correlation between exposure of the cells to the substance and a parallel increase in the expression of surface markers associated with undifferentiation such as SSEA4, SSEA-3, TRA-1-60 (ATCC HB-4783) and TRA-1-81 (ATCC HB-4784), and/or the expression of telomerase. The cells are cultured as described herein. The cells are then exposed to an antibody raised against one or more of the surface markers being screened, and/or the presence or absence of telomerase expression in the exposed cells is determined. In some embodiments, the surface marker antibodies are incubated with a second antibody coupled with a reporter such as a fluorescent label so that cells expressing the appropriate antigenic marker are rendered fluorescent. Labeled cells can then be sorted and counted using standard methods, e.g., a fluorescence-activated cell sorter (FACS). The numbers of labeled and unlabeled cells can then be compared to determine the effect of the putative growth factor. Alternatively, following exposure to unlabeled cell surface marker antibodies, the cells can be exposed to a second antibody that is specific for the cell surface marker antibody in an ELISA (Enzyme-Linked ImmunoSorbent Assay) format from which the number of cells expressing the desired surface antigen can be quantitated colorimetrically or by measurement of fluorescence. Still other methods of quantitating cells expressing surface antigens will be familiar to those having skill in the cell culture arts.

Those substances confirmed to be growth factors can also be tested in combination (e.g., combinations of two or three substances) to determine the presence of any synergistic properties among the growth factors. In addition, substances that may promote differentiation or retard the growth of undifferentiated cells can be identified. For example, antibodies directed to substances in the growth medium can be added to prevent those substances from interacting with the cells being cultured.

Derivatives of Human EG Cells

The methodology and cells of the present invention have a variety of different uses. The cells can be used to study human embryological development. For example, the cells of the invention which exhibit EG cell phenotype can be manipulated with detectably-labeled markers. The marked cells can then be inserted into blastocysts to observe distribution and cell lineages during development of the embryo.

Some additional advantages of using the cells of the invention which exhibit a pluripotent embryonic germ cell phenotype are as follows: A transgene of interest is introduced into an EG cell or EG cell line of the present invention by electroporation, calcium phosphate, microinjection, lipofection, retro- or other viral or microbial vector or other means and its integration and expression characterized in vitro. The effect of the introduced gene on the transformed EG cell is then studied in vitro. The site in the EG cell genome at which the introduced gene integrates can then be manipulated, for gene targeting and gene replacement (Thomas & Capecci. *Cell* 51:503–512, 1987).

The EG cells of the invention can allow the same types of powerful experimental manipulation currently available with mouse ES and EG cells. In one aspect of the invention, stable genetic modifications are made to the EG genome. One example of this is gene replacement and repair through homologous recombination (Thomas & Capecci. *Cell* 51: 503–512, 1987, Capecchi, *Science*, 244: 1288–1292, 1989; Doetschman et al., *Nature*, 330:576–578, 1987). DNA constructs consisting of human DNA flanking the region to be replaced, repaired, augmented, or in any other way altered, along with DNA which contains the altered region and DNA which codes for positive and negative drug selection expression cassettes is transferred to EG cells. This can be done, e.g., by electroporation, calcium phosphate, microinjection, lipofection, retro- or other viral or microbial vector or other means. Cells in which the DNA constructs have undergone homologous recombination are isolated and detected using standard techniques of genomic Southern blotting and polymerase chain reaction.

Stable genetic modification of the EG genome by the addition of homologous or heterologous DNA is another aspect of the invention. DNA constructs containing normal or modified human genes or chromosomal regions, or combinations of human, other animal, and wholly artificial genes, along with genetic elements which allow propagation in a suitable bacterial, yeast, or animal cell host are transferred to EG cells. This is done by electroporation, calcium phosphate, microinjection, lipofection, retro- or other viral or microbial vector or other means. Cells in which the DNA construct(s) have integrated into the EG genome or are stably maintained as an episome are detected using standard techniques such as Southern blotting and polymerase chain reaction (PCR). Yeast artificial chromosome (YAC) mediated insertion of a portion of human chromosome 21 into mouse ES cells is one example of the insertion of a large chromosomal region into a genome (Lamb et al., *Nature Genetics*, 5:22–30, 1993). Other vectors that can be used to add homologous or heterologous DNA to a genome are bacterial artificial chromosomes (BAC), P1 derived artificial chromosomes (PAC), cosmids, bacteriophage or plasmids, and retroviral vector (Helgason et al., *Blood*, 87:2740–2749, 1996). For large-scale addition of DNA to a genome, human artificial chromosomes (HACs) constructed of alpha satellite DNA, telomeric DNA, and genomic DNA (Harrington et al., *Nature Genetics*, 15:345–355, 1997) can be introduced into EG cells.

In another embodiment and use of the invention, human EG cells are genetically manipulated with constructs comprised of reporter molecules such as β-galactosidase, luciferase, or chloramphenicol acetyl transferase (CAT). These constructs can include tissue- or developmental-specific promoters, so that aspects of differentiation can be studied. Random integration of promoter- or enhancerless reporter constructs into the EG genome followed by differentiation can allow discovery of new human gene promoters and enhancers. Reporter constructs with tissue- or, development specific, or constitutive promoters can be used to trace the integration and survival of implanted EG or differentiated or differentiating derivatives.

Controlled Differentiation of Human EG Cells

EG cells can differentiate in vitro into a wide variety of cell types, including embryonic and more highly differentiated cell types. For example, to induce differentiation in monolayer cultures, EG cells are cultured for 2 weeks without passage onto a fresh feeder layer. To induce differentiation in suspension culture, the cells are passed onto a gelatinized plate to eliminate possible contamination by fibroblasts. After 4 to 7 days in culture, colonies are gently dislodged from the plate and disaggregated after incubation in 0.25% trypsin-EDTA for 10–15 min. Dissociated cells are cultured in a microdrop of EG culture medium containing 0.3 µM retmoic acid on a 35-mm nonadhesive petridish. Suspension cultures are monitored daily for embryoid body formation which is indicative of a differentiated phenotype. (Similar experiments testing for differentiation of attached EG cells are well known to those in the art.) Cell culture media is changed every other day.

The EG cells of the invention can be differentiated into various more differentated cell types, some of which are listed below. A broadly applicable method of obtaining pure populations of specific cell types during EG cell differentiation involves the use of a cell-type specific promoter driving a selectable marker gene (e.g., one providing resistance to an otherwise toxic drug). Under the appropriate differentiation conditions, in the presence of the drug, only those cells that can activate the selectable marker (those undergoing the desired differentiation) survive.

Neuroepithelial Cells

In another example, neuroepithelial cells are generated and used to augment or replace cells damaged by illness, autoimmune disorders, accidental damage, or genetic disorder. Mouse ES cells can be induced to differentiate in vitro with retinoic acid to form neuronal and glial precursors, positive for astrocyte (GFAP) or oligodendrocyte (O4) markers, then later into functional neurons (Fraichard et al., *J. Cell Science* 108:3161–3188, 1995). Cells transplanted to adult brains were observed innervating the host striatum (Deacon et al., *Exp. Neurology*, 149:28–41, 1998). Human and mouse EC cell lines can also differentiate into neurons. (Trojanowski et al., *Exp. Neurolog*, 144:92–97, 1997;

Wojcik et al., *Proc. Natl. Acad. Sci. USA.* 90:1305–1309, 1993). Transplantation of these neurons into rats subjected to cerebral ischemia promoted a degree of functional recovery (Borlongan et al., *Exp. Neurology*, 149:310–321, 1998).

It has been demonstrated that expression of the SV40 T antigen (Tag) allows proliferation of precursor cells, and that normal differentiation can resume upon repression of Tag (Lei et al., *Mol. Endocrinol.* 6:703–712, 1992; Lew et al., *Genes Dev.* 7:683–693, 1993; Alarid et al., *Dev.* 122:3319–3329, 1996). The use of inducible expression systems (e.g., the tetracycline-inducible promoter system) or specific deletion of the overexpression construct through a Cre/lox recombination event would allow resumption of the normal differentiation sequence after appropriate expansion of the neuroepithelial precursors.

The present invention provides for the modification and/or differentiation of EG cells for the production of neuronal stem cells using the gene modification techniques and strategies described above. Two overlapping strategies can be used to obtain expanded populations of neuroepithelial precursor cells: (1) the use of culture conditions effective to induce neuroepithelial precursor cell formation from EG cells, and (2) genetic approaches to increasing the yield of neuroepithelial precursors.

In one embodiment, the present invention provides methods and materials to produce neuroepithelial stem cells from EG cells. Embryoid bodies are allowed to replate in insulin-transferin-selenium-fibronectin (ITSN) supplemented medium, a medium which is effective in inducing neuronal differentiation in embronal carcinoma cells (Rizzino and Growley, 1980). These cells are cultured for 6–7 days in the same medium, dissociated and replated into medium containing basic fibroblast growth factor (bFGF). Upon removal of FGF, neurons, astrocytes, and oligodendrocytes are expected to form in situ.

The ability to transfect undifferentiated embryonic stem cells also permits a genetic approach to neuroepithelial precursor cell derivation and expansion. As described previously, the use of cell-type specific promoters driving drug resistance genes allows the selection of specialized cells during EG cell differentiation. Accordingly, if the undifferentiated EG cells are stably transfected with a selectable marker, such as a nestin promoter/neo$^+$ construct, the use of the culture conditions described above combined with drug selection can provide a significant enrichment for neuroepithelial cell precursors.

Hematopoietic Progenitor Cells

EG cultures can also give rise to hematopoietic progenitor cells (Rich, *Blood*, 86: 463–472, 1995). EG-derived hematopoietic cells can be generated and used to augment or replace cells damaged by illness, genetic disorder, or as an alternative to the use of bone marrow transplantation when indicated. Mouse ES cell embryoid bodies form blood islands (Doetschman et al., *J. Embryol. Exp. Morph.*, 87:27–45, 1985) capable of the generation of lymphoid and myeloid mixed-cell populations (Chen et al., *Proc. Natl. Acad. Sci. USA*, 89:2541–2545, 1992). The in vitro derivation of hematopoietic cells from mouse ES cells is enhanced by addition of stem cell factor (SCF), IL-3, IL-6, IL-11, GM-CSF, EPO, M-CSF, G-CSF, LIF, and recapitulates mouse E6.5 to 7.5 hematopoetic development (Keller et al., *Mol. Cell Biol.*, 13:473–486, 1993; Kennedy et al., *Nature*, 386(6624):488493, 1997; Biesecker et al., *Exp. Hematology*, 21:774–778, 1993). Murine ES cells can also generate hematopoietic stem cells (thyl$^+$, SCA-I$^+$, c-kit receptor$^+$, lineage restricted marker negative (B-220, Mac-1, TEN 119, JORO 75, for B-lymphocyte, myeloid, erynhroid, T-lymphocyte, respectively) when cultured on a stromal cell line in the presence of IL-3, IL-6 and fetal liver stromal cell line cultured supernatant). In vitro hematopoiesis is also stimulated by overexpression of HOXB4 (Palacios et al., *Proc. Natl. Acad. Sci. USA.* 92:7530–7534, 1995. Using similar methods, human EG cells can be induced to differentiate and form hematopoietic progenitor cells.

Cardiomyocytes

In another example, human EG-derived cardiomyocytes are generated. Murine embryonic stem (ES) cells can be induced to differentiate in vitro to form cardiomyocytes (Wobus et al., *Differentiation* 48:173–182, 1991; Maltsev et al., *Mech Dev.* 44:41–50, 1993; Klug et al., *J. Clin. Invest.*, 98(1):216–224, 1996). These ES cell-derived cardiomyocytes express appropriate cardiac-specific genes including sarcomeric myosin, desmin, myosin heavy chain, and dystrophin. The cells are electrically coupled and show action potentials typical of atrial, ventricular, and sinus node cardiomyocytes). These cardiomyocytes exhibit spontaneous and rhythmic contractions for as long as 11 months in culture (Klug et al., *J. Clin. Invest.*, 98(1):216–224, 1996). Spontaneous formation of cardiomyocytes derived from primate ES cells in vitro has been observed.

EG cells of the invention can be maintained in the undifferentiated state by culture on primary embryonic fibroblast feeder layers as described above. Using the methods and materials described herein, conditions can be determined to induce substantially specific differentiation of the human EG cells of the invention into cardiomyocytes. In one embodiment, to induce cardiomyocyte differentiation, EG cells are detached from feeder layers and plated in suspension in bacteriological culture plates in typical EG medium in the absence of leukemia inhibitory factor. Under such conditions, the cells form three-dimensional structures called embryoid bodies and begin to demonstrate the formation of multiple differentiated cell types (Doetschman, supra). After 3–7 days growth in suspension, the embryoid bodies are replated onto typical tissue culture dishes and allowed to attach. Spontaneously contracting regions are readily identified and can be isolated, dissociated, and re-plated. In the murine system, these techniques resulted in an overall cardiomyocyte yield of 3–4% (Klug et al., *J. Clin. Invest.*, 98(1):216–224, 1996).

Because EG cells require feeder layers for growth, it may be advantageous to first allow extensive overgrowth of the EG cells on the feeder layers, thereby forming 3 dimentional structures analogous to embryoid bodies, then trypsinize and replate to obtain larger yields of cardiomyocytes.

EG-derived cardiomyocytes can be purified further by the use of cardiomyocyte specific promoters driving, a selectable marker, e.g., the α-cardiac myosin heavy chain (MHC) promoter fused to the aminoglycoside phosphotransferase (neomycin resistance) gene. Undifferentiated EG cells can be transfected with the α-MHC/neo$^+$ construct, grown as embryoid bodies detailed herein, then plated onto tissue culture dishes in the presence of the drug G418. Under these conditions essentially pure populations of cardiomyocytes can be isolated (Klug et al., *J. Clin. Invest.*, 98(1):216–224, 1996). Given the ability to modify by transfection and expand undifferentiated EG cells, large quantities of pure, fully functional cardiomyocytes can be derived. In addition, distinct types of cardiomyocytes show different patterns of gene expression (e.g., myosin light chain (MLC) 2a is expressed in atrial but not ventricular cardiomyocytes; MLC-2v has the complementary pattern of expression ( ) Klug et al., *J. Clin. Invest.*, 98(1):216–224, 1996). The use of a subtype-specific promoter driving a selectable marker gene can allow the isolation of pure populations of specific cardiomyocytes.

Skeletal Muscle Cells

In another example, skeletal muscle cells can be generated. Murine ES cells can be induced to differentiate into skeletal muscle by culture as embryoid bodies in the presence of $10^{-8}$ to $6^{-7}$ M retenoic acid (Wobus et al., *Roux's Arch. Dev. Biol.* 204:36–45, 1994). The application of such conditions to EG cell culture allows derivation of skeletal muscle. Alternatively, using the methods and materials described herein, stably transfected undifferentiated EG cells including an inducible MyoD1 construct can be formed. MyoD1 is a basic helix-loop-helix protein which has the ability to induce muscle gene expression in a variety of cell types (Weintraub et al., *Proc. Natl. Acad. Sci USA* 86:5434–5438, 1989). It has been demonstrated that transfection of murine ES cells with MyoD1, coupled with culture as embryoid bodies in the presence of DMSO, results in efficient formation of skeletal muscle (Dinsmore et al., *Cell Transplant* 5:131–143, 1996). Thus, induction of skeletal muscle by retenoic acid or the formation of human EG cells including an inducible MyoD1 construct allows the growth of large quantities of skeletal myocytes. These cells can also be grown in coculture with EG-derived neurons to provide neuromuscular junctions as described below.

Neuronal Networks

Neuronal networks derived from dissociated mouse embryos have been created on microelectrode arrays; these networks can show coordinated and quasi-periodic firing patterns which respond to the presence of pharmacological agents by altering both the amplitude and the frequency of the burst patterns (Gopal and Gross, *Acta Otolaryngol* (Stockh) 116:690–696, 697–704, 1996). Murine ES cell-derived neurons form both excitatory and inhibitory synapses in culture; these synapses form spontaneously upon differentiation (Okabe et al., supra; Finley et al., *J. Neurosci.* 16:1056–1065, 1996). The higher the density, the more frequent the likelihood of synapse formation.

Using the above-described methods for forming neurons from human EG cells, human EG-derived neurons can be coupled with microelectrode arrays using standard methods and materials. The human EG-derived neuronal cells are expected to form functioning neural networks. Such networks can be used to screen for pharmacological agents, the study of genetic conditions (using, e.g., genetically modifed EG cells as described above) and disease states.

Neuromuscular Junctions

The EG cells provided by the present invention are useful in the development of neuromuscular junctions. The neuromuscular junction is a specialized interaction between nerves and muscles that results in efficient synaptic transmission. This specialized synapse is the target of chemical and biological toxins such as those that exert their effect by inhibition of the enzyme acetylcholinesterase. This enzyme is normally responsible for the degradation of the neurotransmitter acetylcholine, thereby attenuating the stimulation of the muscle by the nerve. The cells of the neuromuscular junction exhibit measurable electrical membrane potentials and depolarization events which are extremely sensitive to perturbations in their micro-environments. Using the methods and materials provided herein, neuromuscular junctions that are uniform can be produced in constant supply without any substantial drift in performance characteristics or sensitivity. Because they are of human origin, they represent the appropriate distribution of membrane receptors and biological response patterns characteristic of human beings. This can be done by the coculture of EG-derived skeletal myocytes and EG-derived neurons as described above. Thus, the EG cells of the invention can provide neuromuscular junctions which can be used, inter alia, to detect toxins, study diseases, and screen for drugs.

Biosensors and Methods of Screening

In another embodiment of the invention, EG cells or their differentiating or differentiated derivatives can be used for toxicological, mutagenic, and/or teratogenic in vitro tests and biosensors. These can replace various animal models, and form novel human based tests and extreme environment biosensors.

In another embodiment or use of the invention, EG cells or their differentiating or differentiated derivatives can be used to build physiological biosensors. These implanted bio-electronic devices could function as in vivo monitors of metabolism and other biological function, or as an interface between human and computer.

In another embodiment, the invention provides a method for identifying a compound which modulates an EG function in some way (e.g., modulates differentiation, cell proliferation, production of factors or other proteins, gene expression). The method includes: a) incubating components comprising the compound and EG cell(s) under conditions sufficient to allow the components to interact; and b) determining the effect of the compound on the EG cell(s) before and after incubating in the presence of the compound. Compounds that affect EG cell function include peptides, peptidomimetics, polypeptides, chemical compounds and biologic agents. Differentiation, gene expression, cell membrane permeability, proliferation and the like can be determined by methods commonly used in the art. The term "modulation" refers to inhibition, augmentation, or stimulation of a particular EG cell function.

Incubating includes conditions which allow contact between the test compound and the EG cell or cells. Contacting can be done under both in vitro and in vivo conditions. For example, it may be desirable to test an array of compounds or small molecules on a single or few EG cells on a "chip" or other solid support. For example, cardiomyocytes or neurons on chips would give a readout of the rate of contraction or number of firings, respectively, in response to a compound and for the detection of harmful or at least biologically active environmental agents.

Neuronal biologically compatible electrode arrays allow the stem cells to undergo further differentiation on the array itself. These arrays, allow the measurement of real time changes in electrical activity in the EG-derived neurons in response to the presence of known or unidentified agents. The electrical activity of cardiomyocytes can be monitored by plating the cells on an array of extracellular microelectrodes (Connolly et al., *Biosens. Biores.* 5:223–234, 1990). The cells show regular contractions, and the extracellular signal recorded showed a relationship to intracellular voltage recordings (Connolly et al., supra). This noninvasive method allows long term monitoring and is simpler and more robust than typical whole cell patch clamp techniques.

The test compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (Saiki et al., *Bio/Technology*, 3:1008–1012, 1985), allele-specific oligonucleotide (ASO) probe analysis (Conner et al., *Proc. Natl. Acad. Sci. USA*, 80:278, 1983), oligonucleotide ligation assays (OLAs) (Landegren et al., *Science*, 241:1077, 1988), and the like. Molecular techniques for DNA analysis have been reviewed (Landegren et al., *Science*, 242:229–237, 1988).

In another aspect, cells cultured or modified using the materials and methods provided by the present invention are mounted to support surfaces to screen for bioactive substances. In one example, the cells are coupled with a substrate such that electrophysiological changes in the cells in response to external stimuli can be measured, e.g., for use as a high-throughput screen for bioactive substances. The cells can be transfected with DNA that targets, expresses, or knocks-out specific genes or gene products in the cell. By providing such chip-mounted cells coupled with measuring devices, such as a computer, many compounds can be screened rapidly and accurately. The biosensor could also be coupled to the measuring device in arrays for large-scale parallel screening.

The biosensor provided by the present invention can also be used to screen for, or warn of, environmental toxins or exposure to dangerous chemicals. In one embodiment, the above-described biosensor is exposed to environmental substances (e.g., air, water, soil), or to samples derived therefrom, and the response of the biosensor is monitored. If a dangerous agent is detected, the response of the system to the agent can be recorded for evaluation, a portion of the sample can be isolated for further study, and an alarm sounded.

Stem Cell Engraftment Potential of EG Cells

In another aspect, the determination of telomerase activity in differentiated derivatives of a modified EG cell is used to determine the Engraftment potential of EG cells cultured using the methods and materials of the present invention. EG cells cultured using the methods and materials of the invention are stably transfected to express the components of telomerase and allowed to differentiate, or, alternatively, induced to differentiate, to produce pluripotent daughter cells such as hematopoietic stem cells for use in transplantation. Induction of differentiation can be performed as described here, including using agents effective to induce differentiation such as retinoic acid. The cells may carry additional genetic modifications using the methods herein. Cells identified as having strong telomerase expression can be specifically isolated and used for transplantation or further culturing and/or modification as described above.

Disease Models

In another use of the invention, EG cells or their differentiating or differentiated derivatives can be used as in vitro models for human genetic diseases. Genetic manipulations are made then the cells are allowed to differentiate. The effect(s) of manipulation can then be studied. These cells will be especially useful for the study of polygenic and contiguous gene disorders, where large-scale or serial manipulations are required. One example of this is the study of human globinopathies by introduction of mutation then study of the cells as they differentiate into hematopoietic cells. Other examples are the study of muscular defects and neuronal defects.

In another use of the invention, unmodified or genetically modified EG cells or their differentiating or differentiated derivatives, are used for human transplantation in the fetus, newborn, infant, children, and/or adult. One example of this use is therapeutic supplementation of metabolic enzymes for the treatment of autosomal recessive disorders. Production of homogentisic acid oxidase by transplanted EG or differentiated derivative cells into the liver could be used in the treatment of alkaptonuria (for review of this disorder, see McKusick, *Heritable Disorders of Connective Tissuie*. 4th ed., St. Louis, C. V. Mosby Co., 1972). Likewise, ornithine transcarbamylase expression could be augmented to treat the disease caused by its deficiency. In another example, glucose-6-phosphate dehydrogenase expression could be augmented in erythrocyte precursors or hematopoietic precursors to allow expression in red blood cells in order to treat G6PD deficiency (favism, acute hemolytic anemnia). Treatments of some diseases require production of a circulating factor. One example is the production of $\alpha_1$-antitrypsin in plasma to treat a deficiency that causes lung destruction, especially in tobacco smokers. Other examples of providing circulating factors are the production of hormones, growth factors, blood proteins, and homeostatic regulators.

In another use of the invention, EG or their differentiating or differentiated derivatives are used to repair or supplement damaged tissues or organs. This may require that EG are first differentiated in vitro into lineage-restricted stem cells or terminally differentiated cells. One example of this is differentiation of EG into vascular cells and channels, then used to repair or create veins and arteries. Mouse ES cell embryoid bodies have been shown to form vascular channels (Wang et al., *Development* 114:303–316, 1992), and this in vitro development can be enhanced with angiogenic factors (Doetschman et al., *Hypertension*, 22:618–629, 1993).

One example of the use of genetic manipulation on EG cells is the reduction or removal of cell-surface molecules responsible for transplantation rejection in order to generate universal donor cells. The mouse Class I histocompatibility (MHC) genes can be disabled by targeted deletion or disruption of the $\beta$-microglobulin gene (Zijlstra et al., *Nature*, 342:435–438, 1989). This significantly improves renal function in mouse kidney allografts (Coffman et al., *J. Immunol.*, 151:425 435, 1993) and allows indefinite survival of murine pancreatic islet allografts (Markmann et al., *Transplantation*, 54:1085–1089, 1992). Mice with a deleted or disrupted $\beta$-microglobulin gene develop normally (Koller et al., *Science*, 248:1227–1230, 1990). Deletion of the Class II MHC genes (Cosgrove et al., *Cell*, 66:1051–1066, 1991) further improves the outcome of transplantation. However, mice lacking both Class I and class II can reject allogenic skin grafts (Grusby et al., *Proc. Natl. Acad. Sci. USA*, 90:3911–3917, 1993). The molecules TAP1 and Ii direct the intercellular trafficking of MHC class I and class II molecules, respectively (Toume et al., *Proc. Natl. Acad. Sci. USA*, 93:1464–1469, 1996). Removal of these two transporter molecules, or other MHC intracellular trafficking systems may also provide a means to reduce or eliminate transplantation rejection. As an alternative to a universal donor approach to histocompatibility, genetic manipulation could be used to generate "custom" MHC profiles to match individual need.

The invention provides methods to generate cells and tissues from EG lines for human transplantation. Towards that end, it may be necessary to eliminate or reduce cell-surface marker molecules on donor transplantation cells or tissues that induce organ graft rejection. The present invention encompasses all such modifications that reduce or eliminate organ graft rejection when employing cells, cell lines (or any parts or derivatives thereof) derived from the EG cells of the present invention. These molecules, termed HLA antigens in humans, comprise MHC class I and II membrane glycoproteins. For non-hematopoietic cells and tissues, elimination or reduction of MHC class I molecules is accomplished by targeted knockout of the human $\beta_2$-microglobulin gene, has been accomplished with mouse ES cells (Zijlstra et al., *Nature* 342:435–438, 1989). Non-hematopoietic cells do not normally produce MHC class II molecules. For hematopoietic cells, the presence of MHC class II glycoproteins may be reduced or eliminated by targeted knockout of the HLA-DP, -DQ, and -DR loci, which are analogous to knockouts of the E and A loci in mouse ES cells (Cosgrove et al., *Cell* 66:1051–1066, 1991).

In another use of the invention, EG cells or their differentiating or differentiated derivatives are used for the generation of organs arid tissues for transplantation. The complexity of this use will likely require combinations of genetic modification, in vitro differentiation, and defined substrate utilization in order to generate the three-dimensional architecture required for functionality. For example, a replacement organ may require vasculature to deliver nutrients, remove waste products, and deliver products, as well as specific cell-cell contacts. A diverse cell population will be required to carry out these and other specialized functions, such as the capacity to repopulate by lineage-restricted stem cells.

In another use of the invention, EG cells or their differentiating or differentiated derivatives can be used for the generation of non-cellular structures such as bone or cartilage replacements.

In another use of the invention, EG cells or their differentiating or differentiated derivatives can be used for transplantation to non-human animals. If desired, such cells may be genetically modified for purposes of gene therapy.

In another use of the invention, EG cells or their differentiating or differentiated derivatives can be used as a source of genetic material such as nuclei, genomic DNA, chromosomes, genes, RNA, and cDNAs. These materials can be used to construct libraries and screening arrays used to discover markers of pluripotency and of differentiation.

In another use of the invention, EG cells or their differentiating or differentiated derivatives can be used as a source of unmodified or genetically modified organelles such as nuclei and mitochondria.

In another use of the invention, EG cells or their differentiating or differentiated derivatives can be used as a source of cells to develop antibodies useful in the study of early human development. Intact wild type, genetically altered, physically or biochemically altered, or differentiated cells or their membrane extracts can be used as immuogen for the formation of mono- or polyclonal antibodies to cell surface molecules.

In one aspect of the invention, the pluripotent EG cell lines offer a valuable paradigm for the immunohistological investigation of early human development by using, monoclonal antibodies specific for cell surface glycolipids (Chiquoine, A.D., *Anal. Rec.*, 118:135–146, 1954: Evans. M. J., and M. H. Kaufman, *Nature* 292:154–156) and glycoproteins (Hogan, B. L. M., U.S. Pat. No. 5,453,357) of the cells of the present invention. These reagents are developed by immunization of mice with mouse and human teratocarcinoma cell lines, as well as mouse embryos. A number of monoclonal antibodies which bind to embryonic cell surface epitopes have been produced in this manner, and are important in the elucidation of glycosylation pathways during development. Monoclonal antibodies which bind to cell surface glycolipids and glycoproteins have been used to study human germ cell tumors (Labosky et al., *Development* 120:3197–3204, 1994; Matsui et al., *Nature* 353:750–751, 1991) and other cancers (Resnick et al., *Nature* 359:550–551, 1992; Thomson et al., *Proc. Natl. Aca. Sci. USA* 92:7844–7848, 1995).

To generate human specific embryonic cell surface antibodies, mice are immunized weekly with about $10^6$ to $10^7$ EG cells, and tail-bled weekly to test for reactivity to EG cells. After reactive sera is detected, hybridomas are produced as described (Andrews et al., *Hybridoma* 3:347–361, 1984) or by standard methods. Resultant monoclonal antibodies are screened against a panel of human cell lines including EG and EC, as well as tissue sections from a variety of germ cell tumors and normal human tissues. Mouse ES, EG, and EC lines are also examined. Other methods of making antibody fragments are known in the art. (See for example, Harlow and Lane, *Antibodies: A Laboratory Manual*, Cold Spring Harbor Laboratory, New York (current edition), incorporated herein by reference).

Another use of EG is in the biosynthetic production of macromolecules. Non-limiting examples of products that could be produced are blood proteins, hormones, growth factors, cytokines, enzymes, receptors, binding proteins, signal transduction molecules, cell surface antigens, and structural molecules. Factors produced by undifferentiated, differentiating, or differentiated EG would closely simulate the subtle folding and secondary processing of native human factors produced in vito. Biosynthetic production by EG involves the genetic manipulation followed by in vitro growth and/or differentiation. Biosynthetic products can be secreted into the growth media or produced intracellularly or contained within the cell membrane, and harvested after cell disruption. Genetic modification of the gene coding for the macromolecule to be biosynthetically produced can be used to alter its characteristics in order to supplement or enhance functionality. In this way, novel enhanced-property macromolecules can be created.

Additionally, the EG cells or cell lines of the invention are a source of RNA for the construction of early development and human pluripotent embryonic germ cell cDNA libraries. Gene expression during the early stages of human development, and in cells which retain pluripotency, has traditionally been difficult to study due to the scarcity of pertinent nucleic acid, molecules, cells and tissues. Using the techniques of the present invention, one of ordinary skill in the art can overcome these difficulties by generating stage specific human nucleic acid, molecules, cells, tissues and genetic material.

Pharmaceuticals, diagnostics, or antibodies, used in manufacturing or processing, are also produced using cells of the present invention. Exogenous foreign or homologous DNA is transferred to EG cells by electroporation, calcium phosphate, microinjection, lipofection, retro- or other viral or microbial vector or other means. The EG cells are screened for incorporation of this DNA, or are used in nuclear transfer systems. These proteins or other molecules are harvested from resulting cell cultures for further purification. For example, human blood clotting factors VIII and IX may be produced for treatment of hemophilia.

Non-limiting examples of the following pharmaceutical, therapeutic, processing, manufacturing or compositional proteins that may be produced in this manner include: blood proteins (clotting factors VIII and IX, complement factors or components, hemoglobins or other blood proteins and the like); hormones (insulin, growth hormone, thyroid hormone, gonadotrophins, PMSG, trophic hormones, prolactin, oxytocin, dopamine, catecholamines and the like); growth factors (EGF, PDGF, NGF, IGF and the like); cytokines (interleukins, CSF, GMCSF, TNF, TGFα, TGFβ, and the like): enzymes (tissue plasminogen activator, streptokinase, cholesterol biosynthetic or degradative, digestive, steroidogenic, kinases, phosphodiesterases, methylases, demethylases, dehydrogenases, cellulases, proteases, lipases, phospholipases, aromatase, cytochromes adenylate or guanylate cyclases and the like); hormone or other receptors (LDL, HDL, steroid, protein, peptide, lipid or prostaglandin and the like); binding proteins (steroid binding proteins, growth hormone or growth factor binding proteins and the like); immune system proteins (antibodies, SLA or MHC gene products); antigens (bacterial, parasitic, viral, allergens, and the like); translation or transcription factors, oncoproteins or proto-oncoproteins, milk proteins (caseins, lactalbumins, whey and the like); muscle proteins (myosin, tropomyosin, and the like).

The nucleotide sequence of the transgene may encode a precursor form of the protein ultimately harvested from the transgeric or transformed cells or cell cultures of the present invention. Preferably, expression of the transgene is inducible. Alternatively, cells may be screened by techniques well known to those of ordinary skill in the art to determine the expression of the transgene by using it as a probe for testing mRNA from cell lines.

Production of differentiated cells for replacement, repair or augmentation of damaged, nonfunctional, or impaired cells or tissues are another use provided by the present invention. Exogenous foreign or homologous DNA is transferred to EG cells by electroporation, calcium phosphate, microinjection, lipofection, retro- or other viral or microbial vector or other means. The EG cells are screened for incorporation for this DNA or used in nuclear transfer systems. These cells and/or tissues are harvested from cell cultures, or resulting cell lines for use in repairing or augmenting a defect. For example, cells, cell products, tissues or the products of cell cultures may be used in treating subjects having Parkinson's disease or subjects who have had a heart attack or spinal cord injury.

Cells, tissues or organs with exogenous major histocompatibility or other foreign or endogenous antigens and/or genes that will decrease rejection by the host organism of these transplanted materials are produced by means of the present invention. For example, members of the Fas ligand gene family can be used. Exogenous foreign or homologous DNA is transferred to EG cell phenotype by electroporation, exposure to calcium phosphate, microinjection, lipofection, retro- or other viral or microbial vector, or other means. The EG cells are screened for incorporation of this DNA or expression of antigens, used in nuclear transfer systems, or grown in vitro culture. Molecules, proteins, cells, tissues, organs, fluids, or cell products are harvested from cells, cell lines, cell cultures for xenotransplantation. In this manner, humanized molecules, proteins, cells, cell products, cell constituents, tissues, organs or fluids are possible.

In another use of the invention, EG cells or their differentiating or differentiated derivatives can be used to in the construction and testing of human artificial chromosomes.

EXAMPLES

The following examples are intended to illustrate but not limit the invention. While they are typical of those that might be used, other procedures known to those skilled in the art may alternatively be used.

Example 1

Collection of Human Primordial Germ Cells and Derivation of Embryonic Germ Cells Gonadal anlagen or genital ridges with mesenteries were dissected from 8–11 week LMP (last menstrual period) human aborted fetal material. The genital ridges were rinsed with 0.5 ml phosphate buffered saline solution or other isotonic buffer (PBS 0.21 g/L $KH_2PO_4$; 9 g/L NaCL; 0.726 g/L $Na_2HPO_4 7H_2O$), then placed into 0.1ml 0.05% trypsin-0.53 mM Sodium EDTA solution (BRL) and was cut into small (less than 1 $mm^3$) chunks. The chunks were then further minced with a fine forceps. The tissue was then repeatedly pipetted through a 100 ul pipet tip to further disaggregate the cells.

The tissue and cell suspension was incubated at 37° C. for approximately 5 min., then approximately 3.5 ml EG growth media (defined as: D-MEM, 4500 mg/L D-glucose, 2200 mg/L mM Sodium bicarbonate; 15% ES qualified fetal calf serum (BRL); 2 mM glutamine (BRL); 1 mM Sodium Pyruvate (BRL); 1000–2000 U/ml human recombinant leukemia inhibitory factor (LIF, Genzyme); 1–2 ng/ml human recombinant basic fibroblast growth factor (bFGF, Genzyme); and 10 $\mu$M Forskolin in 10% DMSO)) was added.

Approximately 0.2 ml of the cell suspension was added to each of 16 wells of a 96-well tissue culture plate previously prepared with a sub confluent layer of STO mouse fibroblasts that had been cultured for 3 days in a modified EG growth media that did not contain LIF, bFGF or Forskolin, then irradiated with 5000 rad of gamma irradiation.

The human PGC cells and STO mouse fibroblasts were cultured for a first passage 7–10 days in EG growth media at 37° C. with 5% $CO_2$ at 90% humidity. Growth media was freshly prepared and replaced daily. Alternatively, subconfluent fibroblast cells can be irradiated, then plated into tissue culture plates to form a feeder layer.

The cells were trypsinized as described here, and each well was passaged to 1 well of a 24-well culture dish previously prepared with irradiated STO mouse fibroblasts (90% of the cells) and to 1 well of a 96-well tissue culture plate previously prepared with irradiated STO mouse fibroblasts (10% of the cells).

The cells were cultured with daily replacement of growth media until cells morphology consistent with murine EG cells were observed, typically, 7–30 days with 1 to 4 passages. Depending on the age of the tissue from which the PGCs were obtained, this process could take one or more passages. On the 13th day of culture (3 days after subculture), a subset of cells growing on the 96-well culture dish were fixed and stained for the presence of alkaline phosphatase by using a commercially available diagnostic kit (Sigma Chemicals, product number 86-R). The cells were washed 2 times with phosphate buffered saline (PBS) then fixed for 30 seconds in a mixture of 25 ml citrate solution (18 mM sodium citrate, 9 mM sodium chloride, pH 3.6), 65 ml acetone and 8 ml of 37% formaldehyde. Fixed cells are then incubated in the dark for 15 min. in Alkaline-dye mixture. The cells are then rinsed with deionized water for 2 min. and allowed to dry. Alkaline phosphatase positive PGC and EG cells stain red, while cells that lack alkaline phosphatase activity, such as STO cells, remain clear.

Cells growing on the 24-well plate were passaged four times to expand cell numbers, and multiple frozen stocks from each passage were prepared. Cells were photographed throughout the initial 13 days of culture using phase contrast microscopy and selected cells were processed for alkaline phosphatase staining as described herein.

In an alternate approach, EG cells were isolated using hyaluronidase/collagenase/DNase. Gonadal anlagen or genital ridges with mesenteries were dissected from 8–11 week LMP human aborted fetal material. The genital ridges were rinsed in PBS then placed in 0.1 ml HCD digestion solution (0.01% hyaluronidase type V, 0.002% DNase I, 0.1% collagenase type IV (all from sigma) prepared in EG growth media). Tissues were cut and minced with a fine forceps in a small glass (preferred) or plastic dish then transferred by pipet to a microfuge tube and incubated 1 hour to overnight 37° C. Approximately 1 ml of EG growth media was then added, and the tissue and cell suspension was centrifuged at 500 rpm for 5 min. The tissue and cells were then resuspended in 1–3 ml of EG growth media, and plated into a recipient dish containing a feeder layer as described above.

For subsequent passages, cells were rinsed in PBS then HCD digestion solution was added. Digestion times ranged from 20 min. To 2 hours, and were monitored microscopically to determine completion. Cells were pumped several times with a pipet, then approximately 10 volumes of EG growth media were.added. The tissue and cells were then removed to a tube and centrifuged at 500 rpm for 5 min. The tissue and cells were then resuspended in EG growth media, and plated into a recipient dish containing a feeder layer as described above.

Example 2

Passage of Pluripotent Cells

EG growth media was replaced daily, and the cells were grown at 37° C., 90% relative humidity, 5% $CO_2$ for 4–14 days until cells with morphology consistent to murine EG were observed. At this time, the cells were trypsinized and subcultured to freshly prepared 96-well or 24-well plates with irradiated feeder layer. A subpopulation of these cells were fixed and stained for alkaline phosphatase activity. These cells were passaged at least 4 times over a 40 day period, with continued demonstration of alkaline phosphatase activity as demonstrated by positive staining.

Figure 1B:
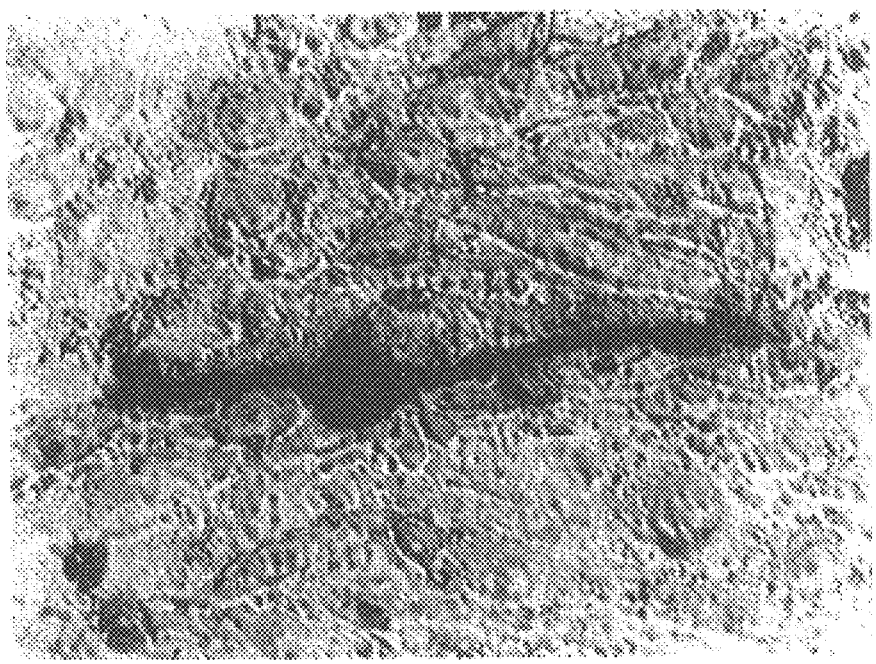
Figure 2A:
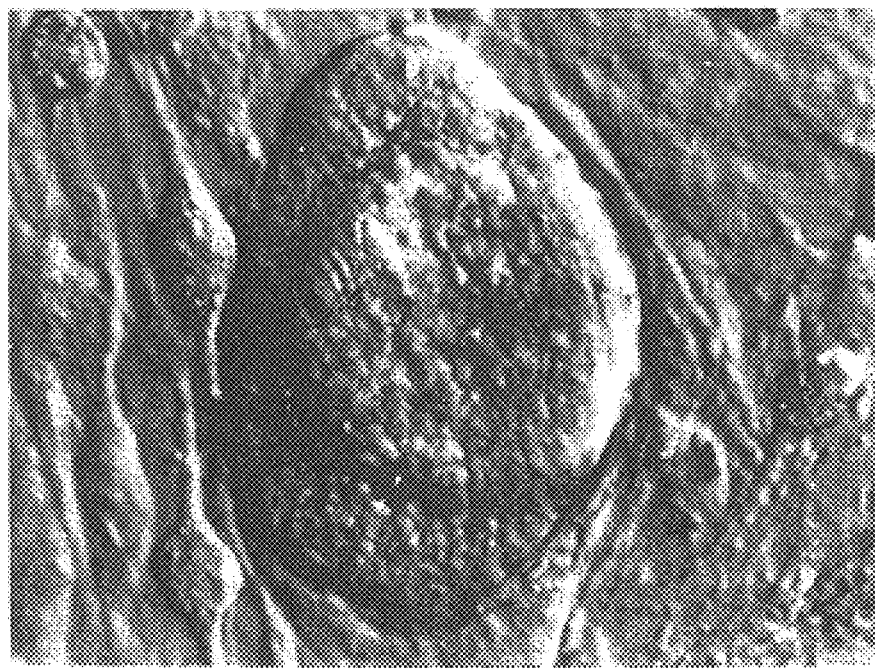
FIGS. 2a and b show photomicrographs of human embryonic germ cell colonies.
Figure 2B:
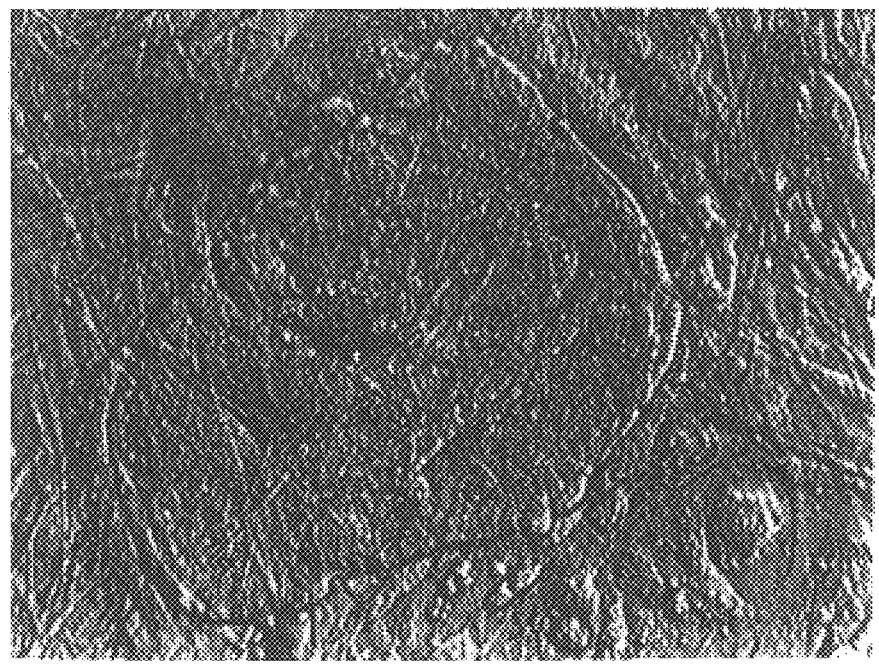

After 1 to 3 passages (7 to 30 days) some cells in the human PGC culture change from isolated and, solitary human PGCs, readily identified only by alkaline phosphatase staining or antibody detection (see FIGS. 1a and 1b), until cell colonies with morphology consistent to murine EG were observed (see FIGS. 2a and 2b). These colonies can be recognized by light microscopy. The human EG cells can be characterized with respect to alkaline phosphatase activity, presence of cell surface antigens, and/ or the ability to form teratocarcinomas in SCID mice. The EG colonies were isolated from the rest of the culture using a cloning cylinder, expanded through repeated passage, then characterized as separate cell lines.

To test for teratocarcinoma formation in SCID mice, a pellet consisting of approximately 500,000 EG cells is injected into the rear leg muscle, testis, or kidney capsule of 8–15 week old SCID mice. After 8–20 weeks of development, the resulting tumors are fixed in 4% paraformaldehyde and embedded in paraffin. Tissue sections are examined using standard histological staining techniques and immunohistochemical detection of cell surface antigens and other epitopes as described herein. The presence of cells from the endoderm, ectoderm, and mesoderm germ layers indicates the cells are pluripotent EG cells.

Example 3

Testing Harvested Cells for Morphology and Alkaline Phosphatase Activity

As previously described, in a preferred embodiment primordial germ cells (PGCs) are harvested from nascent gonadal ridges since their early developmental age inhibits subsequent differentiation and loss of pluripotency.

To ascertain that harvested cells were of an appropriate developmental age, harvested cells were tested for morphological criteria used to identify primordial germ cells that are pluripotent (DeFelici and McLaren, Exp. *Cell.* 142:476–482, 1982). To further substantiate pluripotency a sample of the extracted cells were subsequently tested for alkaline phosphatase (AP) activity. Markers for pluripotent cells are often useful to identify stem cells in culture. EG cells typically manifest alkaline phosphatase (AP) activity and AP positive cells are typically pluripotent. AP activity is rapidly lost with differentiation of EG cells in vitro. AP expression has been demonstrated in ES and ES-like cells in the mouse (Wobus et al., *Exp. Cell* 152:212–219, 1984; Pease et al., *Dev. Bio.* 141:344–352, 1990), rat (Ouhibi et al., *Mol. Repro. Dev.* 40:311–324, 1995), pig (Talbot et al., *Mol. Repro. Dev.* 36:1139–147, 1993b) and cow (Talbot et al., *Mol. Repro. Dev.* 42:35–52, 1995). AP activity has also been detected in murine PGCs (Chiquoine, *Anat. Rec.* 118:135–146, 1954), murine EG cells (Matsui et al., *Cell* 70:841–847, 1992; Resnick et al., *Nature* 359:550–551, 1992), and cultured avian embryonic cells from chickens (Pain et al., *Dev.* 122:1996). In conjunction with morphological evaluation of the EG cell colony, AP expression therefore is a convenient marker to identify pluripotent embryonic germ cells in culture.

Cell samples taken from the EG cell lines cultured as in Example 2 were assessed, using light microscopy, for the presence of morphological criteria indicative of putative EGs. The EGs first appeared either as round cells or round cells with two or more extended pseudopodia when visualized after staining for alkaline phosphatase (AP) activity. After 2–30 days in culture, multicellular colonies of EGs developed. First, 10 to 100 individual cells formed a loosely associated aggregation. In subsequent passages, some colonies became larger and appeared to be comprised of many cell layers. The individual cells of these colonies appeared small and more tightly associated. EG cultures were maintained for greater than 3 months by passage every 4–10 days onto fresh irradiated mouse STO fibroblasts or human lung fibroblasts. After approximately 1 week to 2 months, some EGs formed colonies with larger diameter, but fewer cell layers. The cells demonstrated a tightly clustered and rapidly growing morphology reminiscent of early passage mouse ES and EG cultures.

Figure 3A:
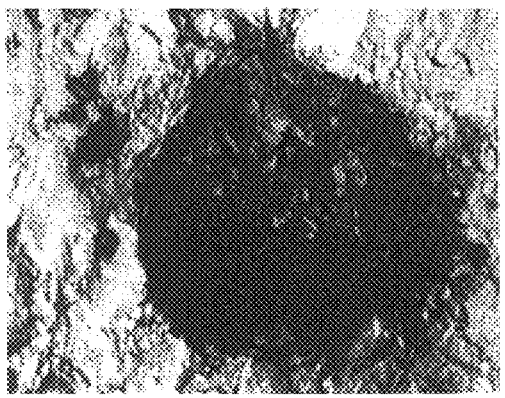
FIG. 3 shows photomicrographs of human embryonic germ cell (EG) colonies showing positive inmmunohistochemical staining for: (A) stage specific embryonic antigen-1 (SSEA-1); (B) stage specific embryonic antigen-3 (SSEA-3); (C) stage specific embryonic antigen-4 (SSEA-4); (D) a cell surface antigen that binds with the antibody having the binding specificity of the monoclonal antibody designated TRA-1-60 (ATCC HB-4783); (E) a cell surface antigen that binds with the antibody having is the binding specificity of the monoclonal antibody designated TRA-1-81 (ATCC HB-4784); (F) alkaline phosphatase activity.
Figure 3D:
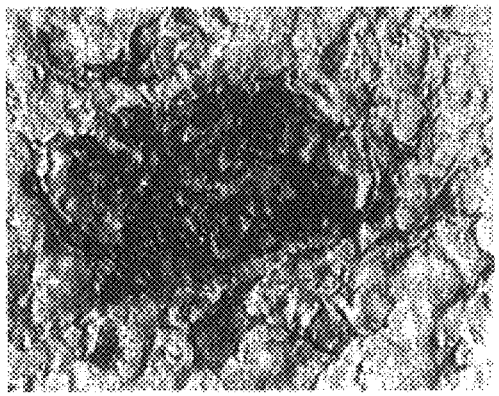
Figure 3B:
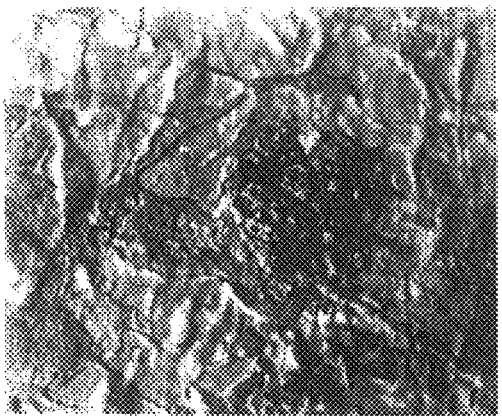
Figure 3E:
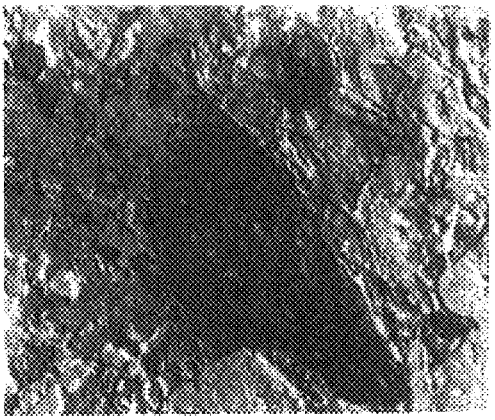
Figure 3C:
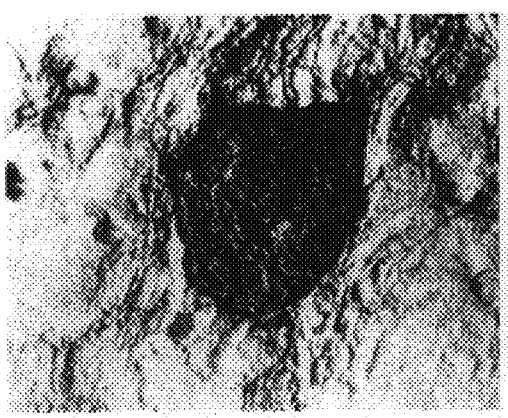
Figure 3F:
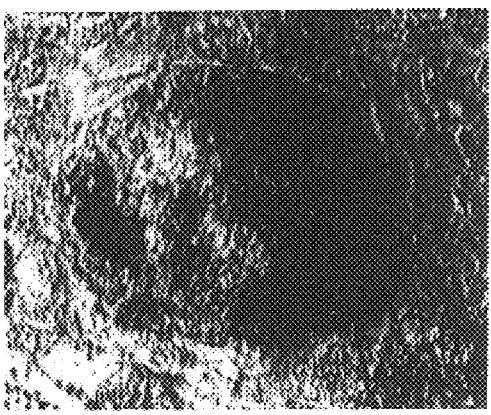

Subsequently, cells were tested for alkaline phosphatase activity by fixing as described in Example 1 and staining them employing a protocol from an AP cyto-chemistry kit (Sigma Chemical Co., St. Louis, Mo.). The results indicated that AP activity was consistently expressed in EGs and in primary cultures and subcultures of EG cells (see FIG. 3F). The cells demonstrated strong and convincing histological staining for alkaline phosphatase. Surrounding STO mouse fibroblasts did not stain for alkaline phosphatase. Therefore, cells testing positive for both morphological criteria and AP activity were consistent with those expected for human EG cells. These cells typically make up 10–50% of all harvested cells, although accurate cell counts are complicated by the tight colonies formed.

Example 4

Pluripotency of EG Determined by Antibody Staining

Other indicators of pluripotency can also be investigated. These include, but are not limited to, the presence of stage specific embryonic antigens such as SSEA-1 (Solter, D. and B. Knowles, *Proc. Natl. Acad. Sci. USA* 75: 5565–5569, 1978), SSEA-3, SSEA-4 (Kannagi, R., et al., *Embo J.* 2:2355–2361, 1983) and epitopes recognized by the antibodies TRA-1-60 (ATCC HB-4783) and TRA-1-81 (ATCC HB-4784) (Andrews, P., et al., *Hybridoma* 3:347–361, 1984), and the ability of these cells to form teratocarcinomas or teratomas when injected into immuno-compromised (SCID) mice.

EG cultures grown on plastic chamber slides were stained with 5 monoclonal antibodies to embryonic cell surface antigens. Cells were rinsed 2 times with phosphate buffered saline (PBS) then fixed in 3% paraformaldehyde for 15 minutes at room temperature. The cells were washed two times in PBS, then incubated in a 1:5 to 1:25 dilution (in PBS) of each of the following monoclonal antibodies for 1 hour at room temperature: TRA-1-81 (ATCC HB-4784) and TRA-1-60 (ATCC HB-4783) (supplied by Dr. Peter Andrews, Sheffield, UK); MC-480 (anti-SSEA-1), MC-631 (anti-SSEA-3), and MC-813–70 (anti-SSEA-4) (anti-SSEA antibodies were supplied by the Developmental Studies Hybridoma Bank, Iowa City, Iowa). The cells were subsequently washed twice in PBS. Biotinylated antimouse immunoglobulin secondary antibody, and horseradish peroxidase-conjugated strepavidin (BioGenex, San Ramon, Calif.) were used as recommended by the manufacturer.

Antibodies to SSEA-1 and -4 antigens and TRA-1-60 (ATCC HB-4783), and -81 (ATCC HB-4784) reacted strongly to the EG cells, while the antibody to SSEA-3 reacted weakly (see FIGS. 3A–3E). The cells also reacted positively for AP. The results are consistent with the characteristics expected for human EG cells.

Example 5

Cultured EG Cells Display Normal Karyotypes

To determine whether the isolate human EG cell lines exhibited normal karyotype, approximately 10–20 metaphase stage karyotypes from each EG cell line were tested by examining the cell's chromosomes for both structural and numerical abnormalities. Five (5) EG cultures were karyotyped and were found to be normal 46,XY and 46,XX. Colonies from these cultures were isolated and expanded two separate times to generate EG lines.

Cells were placed in 4-well culture dishes and cultured overnight in EG culture medium containing 0.02 ug/ml colcemid (GIBCO BRL) at 39° C. in 5% $CO_2$, 95% air. Cells were subsequently washed in PBS, treated with 0.25% trypsin-EDTA for 10–15 minutes at 39° C., removed and centrifuged for five minutes at 800 g. Cells were fixed for five minutes in cold Carnoy's fixative (3:1 volume of absolute methanol to glacial acetic acid), washed in PBS, centrifuged as above, and resuspended in 0.5 ml of Carnoy's fixative. A pipette drop of the resulting cell suspension was transferred onto microscopic slides that were prewashed with Carnoy's fixative. Slides were air dried. Giemsa stained (GIBCO, BRL) and rinsed with tap water. After a second drying, slides were cover slipped and viewed under oil immersion using light microscopy at 400X magnification.

All EG cell lines examined had a normal complement of human chromosomes (i.e., 44 autosomes and 2 sex chromosomes). Additionally, no breaks, deletions, additions or other abnormalities in the shape or number of chromosomes were observed. Among isolated EG cell lines, no obvious differences were observed in morphology, proliferation and AP activity. After 8 to 12 passages, all 4 isolated EG cell lines, the two from cell line hEG-KH and the two from cell line HEG-GU had a normal human complement of 46 chromosomes (44 autosomes and 2 sex chromosomes). No obvious abnormalities, additions or deletions are found in chromosomes from isolated EG cells as described above.

TABLE 1

Characteristics of human EG cell lines

| hEG Cell Line | Collected From | Karyotype (2N) | Passage Number |
| --- | --- | --- | --- |
| KH | 9 week LMP | 46, XX | 20 |
| GU | 11 week LMP | 46, XY | 30 |

Example 6

Culture or EG Cells

In the mouse, pluripotent embryonic stem cells are derived principally from two sources. Embryonic stem (ES) cells are derived from the inner cell mass of preimplantation embryos, while embryonic germ (EG) cells are derived from primordial germ cells (PGCs) located in the genital ridge of day 8.5 to 12.5 post coitum embryo. Both types of cells are pluripotent and demonstrate germline genetic transmission in the mouse. Mouse ES and EG cells share several morphological characteristics such as high levels of intercellular alkaline phosphatase (AP), growth as tightly associated multicellular colonies, presentation of specific cell surface glycolipid and glycoprotein molecules. Some additional characteristics are a normal and stable karyotype and the ability to be continuously passaged. Embryonic stem cells that share some of these characteristics have been derived from avian species, mink, hamster, pig, bovine and the rhesus monkey.

When allowed to differentiate, mouse ES and EG cells will differentiate in vitro and in vivo. With the proper combinations of growth and differentiation factors, they can generate cells of the hematopoietic lineage and cardiomyocytes. Additionally, mouse ES cells have been used to generate in vitro cultures of neurons, skeletal muscle, and vascular endothelial cells. When undifferentiated ES and EG cells are injected into mice (immunocompromised if appropriate), a teratocarcinoma forms at the site. These tumors contain undifferentiated cells and a wide variety of differentiated cell types.

Human pluripotent stem cell cultures and their lineage restricted derivatives could potentially be used as an unlimited source of cells and tissues for transplantation, biomanufacturing, and developmental research. Genetic manipulation of these cells may provide suitable vectors for future gene therapy approaches. In an effort to generate human pluripotent stem cells, we have initiated and characterized a number of cell cultures derived from human PGCs.

Methods

Gonadal ridge and mesenteries of 5–9 week postfertilization human embryos were dissociated with 0.25% trypsin-EDTA and mechanical disruption. Tissues were initially cultured, and subsequently passaged, on an irradiated mouse STO fibroblast feeder layer in DMEM supplemented with 15% FBS, human recombinant leukemia inhibitory factor (hrLIF), human recombinant basic fibroblast growth factor (hrbFGF) and forskolin. For alkaline phosphatase activity detection, cells were fixed in 66% acetone/3% formaldehyde then stained with napthol/FRV-alkaline AP substrate (Sigma). For immunocytochemistry, cells were fixed in 3% buffered paraformaldehyde. Antibody detection was done using biotinylated anti-mouse antibodies, strepavidin conjugated horseradish peroxidase, and AEC chromagen (BioGenex). Cells prepared for cytogenetic analysis were treated with 0.1 ug/ml Colecimd, 0.075M KCl, then 3:1 methanol acetic acid fix.

Results

Pluripotent embryonic stem cell lines have been derived from cultures of mouse primordial germ cells (PGCs), and have been referred to as EG (embryonic term) cells. With the goal of establishing human EG cell lines, gonadal ridge and mesenteries of 5–9 week postfertilization embryos (obtained as the result of pregnancy termination) were cultured on mouse STO fibroblast feeder layers in the presence of a variety of growth factors, including human recombinant leukemia inhibitory factor (hrLIF), human recombinant basic fibroblast growth factor (hrbFGF), and forskolin. Initially, single PGCs were visualized by alkaline phosphatase (AP) staining. Over a period of 7–21 days, these PGCs gave rise to large multicellular colonies resembling those of early passage mouse EG and embryonic stem (ES) cell colonies. Throughout the culture period and with subsequent passages, the cells continued to be AP positive. The cells were also positive when tested against a panel of five monoclonal antibodies (SSEA-1, SSEA-3, SSEA4, TRA-1-60 (ATCC HB-4783). TRA-1-81 (ATCC HB-4784)) used routinely to characterize pluripotent stem cells. The cultured cells have been continuously passaged and found to be karyotypically normal and stable. Both XX and XY cell cultures have been obtained. The properties so far characterized on the derived human cells are consistent with those anticipated for pluripotent stem cells. (See Table 2)

Several human PGC derived cell cultures have been obtained. All cultures tested have shared the morphological, immunological, and karyotypic characteristics described. In order to compare these cell cultures to ES or EG cells, their potential to differentiate in vitro and in vivo must be determined. During standard culture, a small fraction of colonies spontaneously differentiate into structures that strongly resemble mouse embryoid bodies (EB). When analyzed by electron microscopy, a wide variety of cell types were identified, including an epithelial outer layer covering an partially solid core of fibroblasts, endothelial cells, and what appear to be anucleated red blood cells.

TABLE 2

| Antibody | | | Reactivity | | | |
|---|---|---|---|---|---|---|
| | | | Primate | | | |
| | | | human | | | Mouse |
| Name | Antigen | Antigen type | PGC derived | hEC | mES | EC | ES | EG |
| MC480 | SSEA-1 | glycolipid (lacto) | + | − | − | + | + | + |
| MC631 | SSEA-3 | glycolipid (globo) | ± | + | + | − | − | − |
| MC813-70 | SSEA-4 | glycolipid (globo) | + | + | + | − | +/− | + |
| TRA-1-60 | | glycoprotein | + | + | + | − | − | − |
| TRA-1-81 | | glycoprotein | + | + | + | − | − | − |

Antibody reactivity to primate and mouse cell lines. Abbreviations are as follows: hEC, human embryonal carcinoma; mES, monkey embryonic stem cell; EG, embryonic germ cell.

Although the invention has been described with reference to the presently preferred embodiment, it should be understood that various modifications can be made without departing from the spirit of the invention. Accordingly, the invention is limited only by the following claims.

What is claimed is:

1. A method of producing a cell population comprising differentiating in culture human embryonic germ (hEG) cells, wherein the hEG cells have the following culture characteristics during maintenance:
    (i) dependence on an agent that binds to gp 130 or that binds to a receptor that can associate with gp 130; and
    (ii) dependence on a growth factor.

2. The method of claim 1 wherein the primordial germ cells are from gonadal ridge tissue collected 3 to 13 weeks post-fertilization.

3. The method of claim 1 wherein the agent is selected from the group consisting of oncostatin-M, leukemia inhibitory factor, and an antibody to gp 130.

4. The method of claim 1 wherein the growth factor is basic fibroblast growth factor.

5. The method of claim 1 wherein the hEG cells have been obtained by culturing primordial germ cells in a medium that also contains a factor that elevates intracellular cAMP.

6. The method of claim 5 wherein the factor that elevates intracellular cAMP is selected from the group consisting of forskolin, cholera toxin, isobutylmethylxanthine and dibutyladenosine cyclic monophosphate.

7. The method of claim 1 wherein the hEG cells are differentiated by culturing for at least two weeks without passage onto a fresh layer of feeder cells.

8. The method of claim 1 wherein the hEG cells are differentiated by passaging them into a suspension culture.

9. The method of claim 8 wherein the cell population comprises embryoid bodies.

10. The method of claim 1 wherein the cell population comprises a member of the group consisting of neuroepithelial cells, hematopoietic progenitor cells, cardiomyocytes, and skeletal muscle cells.

11. The method of claim 1 wherein the hEG cells are differentiated by culturing in the presence of a member of the group consisting of retinoic acid, IL-3, IL-6, IL-11, GM-CSF, EPO, M-CSF, and G-CSF, or by withdrawing the growth factor with which the cells have been maintained.

12. A method of producing a population of restricted developmental lineage cells comprising:
    (a) maintaining hEG cells by culturing in a medium comprising a growth factor and an agent that binds to a receptor that can associate with gp 130, wherein the hEG cells have the following culture characteristics during maintenance:
        (i) dependence on an agent that binds to gp 130 or that binds to a receptor that can associate with gp 130; and
        (ii) dependence on a growth factor; and then
    (b) differentiating the hEG cells.

13. The method of claim 12 wherein the hEG cells are differentiated by culturing the hEG cells for at least two weeks without passage onto a fresh layer of feeder cells, or by passaging the hEG cells into a suspension culture.

14. The method of claim 12 wherein the cell population comprises embryoid bodies.

15. The method of claim 12 wherein the cell population comprises a member of the group consisting of neuroepithelial cells, hematopoietic progenitor cells, cardiomyocytes, and skeletal muscle cells.

16. A method for producing human pluripotent embryonic germ (hEG) cells comprising:
    (a) preparing a suspension of primordial germ cells;
    (b) culturing cells of the suspension with feeder cells in a medium comprising a factor that elevates cellular cAMP levels; and
    (c) harvesting pluripotent embryonic germ cells from the culture.

17. The method of claim 16 wherein the factor that elevates cellular cAMP levels is forskolin.

18. A human pluripotent embryogenic germ (hEG) cell prepared according to the method of claim 16.

19. The cells of claim 18, which are alkaline phosphatase positive.

20. The cells of claim 18, which express cell surface antigen SSEA-4, and cell surface antigens that bind with antibodies having the binding specificity of monoclonal antibodies TRA-1-60 and TRA-1-81.

21. The cells of claim 20, which express cell surface antigen SSEA-3.

22. The cells of claim 18, which express cell surface antigen SSEA-1.

23. The method of claim 16, wherein the medium further comprises
   (d) dependence on an agent that binds to gp130 or that binds to a receptor that can associate with gp130; and
   (e) a growth factor.

24. The method of claim 23, wherein the growth factor is basic fibroblast growth factor (bFGF).

25. The method of claim 23, wherein the ligand that binds to a receptor which can associate with gp130 is oncostatin-M or LIF.

26. The method of claim 23, wherein the agent that binds to and activates gp 130 is an antibody.

27. The method of claim 16, wherein the cells that are produced have the following culture characteristics during maintenance:
   (i) dependence on an agent that binds to gp130 or that binds to a receptor that can associate with gp130; and
   (ii) dependence on a growth factor.

28. A method for producing a population of restricted developmental lineage cells, comprising producing hEG cells according to the method of claim 16, and then causing them to differentiate.

* * * * *